(12) United States Patent
Jordan et al.

(10) Patent No.: US 9,089,567 B2
(45) Date of Patent: Jul. 28, 2015

(54) METHOD OF TREATING COGNITIVE IMPAIRMENTS AND SCHIZOPHRENIAS

(75) Inventors: Shaun Jordan, Germantown, MD (US);
Tetsuro Kikuchi, Tokushima (JP);
Katsura Tottori, Kamiita-cho (JP);
Tsuyoshi Hirose, Tokushima (JP);
Yasufumi Uwahodo, Tokushima (JP)

(73) Assignee: Otsuka Pharmaceutical Co., LTD., Tokyo (JP)

( * ) Notice: Subject to any disclaimer, the term of this patent is extended or adjusted under 35 U.S.C. 154(b) by 0 days.

(21) Appl. No.: 13/303,265

(22) Filed: Nov. 23, 2011

(65) Prior Publication Data

US 2012/0172373 A1    Jul. 5, 2012

Related U.S. Application Data

(60) Continuation of application No. 12/830,740, filed on Jul. 6, 2010, now abandoned, which is a continuation of application No. 12/202,192, filed on Aug. 29, 2008, now abandoned, which is a division of application No. 10/876,605, filed on Jun. 28, 2004, now Pat. No. 8,030,312, which is a division of application No. 10/055,915, filed on Jan. 28, 2002, now Pat. No. 7,053,092.

(60) Provisional application No. 60/331,370, filed on Jan. 29, 2001.

(51) Int. Cl.
A61K 31/496     (2006.01)
A61K 45/06      (2006.01)

(52) U.S. Cl.
CPC .............. *A61K 31/496* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,438,119 A | 3/1984 | Allen et al. | |
| 4,687,772 A | 8/1987 | Alderdice et al. | |
| 4,734,416 A | 3/1988 | Banno et al. | |
| 4,771,053 A | 9/1988 | Cott et al. | |
| 4,983,607 A | 1/1991 | Manoury et al. | |
| 5,006,528 A | 4/1991 | Oshiro et al. | |
| 5,073,377 A | 12/1991 | Alexander et al. | |
| 5,162,375 A | 11/1992 | Nicholson et al. | |
| 5,200,410 A | 4/1993 | Traber et al. | |
| 5,385,914 A | 1/1995 | Fujioka et al. | |
| 5,504,093 A | 4/1996 | Gelfand et al. | |
| 5,652,247 A | 7/1997 | Ogawa et al. | |
| 5,691,330 A | 11/1997 | Nakao et al. | |
| 5,824,680 A | 10/1998 | Turner et al. | |
| 6,267,942 B1 | 7/2001 | Mori et al. | |
| 7,053,092 B2 | 5/2006 | Jordon et al. | |
| 8,399,469 B2 | 3/2013 | Bando et al. | |
| 2002/0076437 A1 | 6/2002 | Kothari et al. | |
| 2002/0156067 A1 | 10/2002 | Wong et al. | |
| 2003/0027817 A1 | 2/2003 | Tollefson | |
| 2010/0069317 A1 | 3/2010 | Forino et al. | |
| 2012/0316180 A1 | 12/2012 | Bando et al. | |

FOREIGN PATENT DOCUMENTS

| | | |
|---|---|---|
| AU | 2002226752 B2 | 8/2002 |
| CA | 1117110 A1 | 1/1982 |
| DE | 29 12 105 C2 | 8/1985 |
| DE | 29 12 105 C3 | 8/1985 |
| DE | 29 53 723 C2 | 1/1989 |
| EP | 0 226 441 | 6/1987 |
| EP | 0 360 077 | 3/1990 |
| EP | 0 367 141 | 5/1990 |
| EP | 0 565 274 | 10/1993 |
| EP | 0 776 927 B1 | 6/1997 |
| GB | 2017701 B | 10/1979 |
| JP | 54-130587 | 10/1979 |
| JP | 55-127371 | 10/1980 |
| JP | 56-46812 | 4/1981 |
| JP | 62-149664 | 7/1987 |
| JP | 2-191256 | 7/1990 |
| JP | A-70135 | 3/1995 |

(Continued)

OTHER PUBLICATIONS

"Aripiprazole," Drugs Fut., 25(9):961-963 (2000).

(Continued)

*Primary Examiner* — James D Anderson
(74) *Attorney, Agent, or Firm* — Finnegan, Henderson, Garrett & Dunner, LLP

(57) ABSTRACT

The present invention relates to a method of treating a patient suffering from a disorder of the central nervous system associated with 5-HT$_{1A}$ receptor subtype, comprising as an active ingredient a carbostyril derivative or a salt thereof represented by the formula (1)

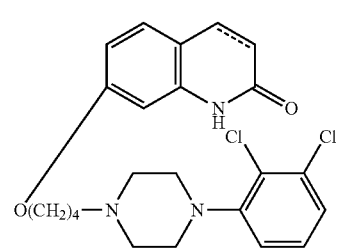

(1)

wherein the carbon-carbon bond between 3- and 4-positions in the carbostyril skeleton is a single or a double bond.

10 Claims, No Drawings

(56) References Cited

FOREIGN PATENT DOCUMENTS

| JP | 07-304740 | 11/1995 |
|---|---|---|
| JP | 9-40648 | 2/1997 |
| JP | 11-508280 | 10/1997 |
| JP | 9-301 867 | 11/1997 |
| JP | 9-291034 | 11/1997 |
| JP | 11-509865 | 11/1997 |
| JP | 11-335286 | 12/1999 |
| JP | 2001-302499 | 10/2001 |
| WO | WO 92/10200 | 6/1992 |
| WO | WO 92/20655 | 11/1992 |
| WO | WO 93/04681 | 3/1993 |
| WO | WO 94/09765 | 5/1994 |
| WO | WO 94/13620 | 6/1994 |
| WO | WO 98/07426 | 2/1998 |
| WO | WO 98/08817 | 3/1998 |
| WO | WO 99/38864 | 8/1999 |
| WO | WO 99/52870 | 10/1999 |
| WO | WO 00/16777 | 3/2000 |
| WO | WO 01/52855 | 7/2001 |
| WO | WO 02/060423 A2 | 8/2002 |
| WO | WO 02/102297 A2 | 12/2002 |
| WO | WO 03/026659 A1 | 4/2003 |
| WO | WO 03/030868 | 4/2003 |

OTHER PUBLICATIONS

Abi-Dargham, "Probing cortical dopamine function in schizophrenia: what can D1 receptors tell us?" World Psychiatry, 2(3):166-171 (2003).
American Psychiatric Association, "DSM-IV Classification for Bipolar Disorders," Quick Reference to the Diagnostic Criteria from DSM-IV, pp. 24-25 (1994).
Bowden, "Novel Treatments for Bipolar Disorder," Exp. Opin. Invest. Drugs, 10(4):661-671 (2001).
Bristol Myers Squibb & Otsuka, Package insert for Abilify® tablets, Sep. 2011.
Citrome & Volavka, "Atypical antipsychotics: revolutionary or incremental advance?" Expert Rev. Neurotherapeutics, 2(1):69-88 (2002).
Cohen et al., "Characterization of the Discriminative Stimulus Produced by the Dopamine Antagonist Tiapride," J. Pharmacol. Exp. Ther., 283:566-573 (1997).
Ebsworth, et al., "Diffraction by powders," Structural Methods in Inorganic Chemistry, Blackwell Scientific Publications, 2nd ed., p. 360 (1991).
English translation of European Patent Office, Communication of a notice of opposition for EP Application No. 06015782.3/ EP Patent No. 1712225, dated Jan. 26, 2012, forwarding HELM AG's Jan. 6, 2012, submission.
European Patent Office submission of Otsuka Pharmaceutical Co., Ltd. during opposition proceedings for European Patent No. 1330249, dated Mar. 6, 2009, including x-ray and DSC spectra for Samples 1 and 2 and p. 939 of D2.
European Patent Office submission of Otsuka Pharmaceutical Co., Ltd. during opposition proceedings for European Patent No. 1419776, dated Apr. 3, 2012, including Declarations 1 and 2 of Mr. Aoki, executed Apr. 2, 2012.
European Patent Office submission of Otsuka Pharmaceutical Co., Ltd. during opposition proceedings for European Patent No. 1419776, dated Aug. 29, 2011, including DSC and XRD data for Type-2 Crystal.
European Patent Office submission of Otsuka Pharmaceutical Co., Ltd. during opposition proceedings for European Patent No. 1419776, dated Feb. 24, 2012, including Annex 1, overview of the powder X-ray diffraction spectra of Type-1, Type-2 and Type-C(Part 1-Part 4) and Annex 2, overview of the powder X-ray diffraction spectra of Type-2 crystals, Sample MT-2178 (Part 1) and PZ-8057-3 (Part 2) and Type-C crystals.
European Patent Office submission of Otsuka Pharmaceutical Co., Ltd. during the appeal of European Patent No. 1330249, dated Nov. 17, 2009, including Experimental Report with Annexes 1-3.
European Patent Office submission of Otsuka Pharmaceutical Co., Ltd. in European Patent Application No. 02782507.4-2101, dated Dec. 15, 2004.
European Patent Office submission of Otsuka Pharmaceutical Co., Ltd. in European Patent Application No. 04002427.5, dated Sep. 8, 2008, including Annexes 1-3.
European Patent Office submission of Otsuka Pharmaceutical Co., Ltd. in European Patent Application No. 06015782.3, dated Aug. 19, 2010.
European Patent Office submission of Otsuka Pharmaceutical Co., Ltd. in European Patent Application No. 06015782.3, dated Nov. 13, 2008, including Comparative Experiments.
European Patent Office submission of Otsuka Pharmaceutical Co., Ltd. in European Patent Application No. 08000357.7-2101, dated Mar. 5, 2009, including Annexes 1-3.
European Patent Office submission of Otsuka Pharmaceutical Co., Ltd. in European Patent Application No. 08000358.5, dated Apr. 27, 2009, including Annexes 1-3.
European Patent Office submission of Otsuka Pharmaceutical Co., Ltd. in European Patent Application No. 08000359.3-2101, dated Mar. 5, 2009, including Annexes 1-3.
European Patent Office submission of Otsuka Pharmaceutical Co., Ltd. in European Patent Application No. 08000360.1-2101, dated Mar. 5, 2009, including Annexes 1-3.
European Patent Office submission of Otsuka Pharmaceutical Co., Ltd. in the appeal of European Patent No. 1621198, dated May 27, 2011, including Affidavit of Bryan L. Roth, M.D., Ph.D., executed May 23, 2011.
European Patent Office submission of Teva Pharmaceutical Industries Ltd. in opposition to European Patent No. 1419776, dated Apr. 16, 2012.
European Patent Office, Communication of a notice of opposition for EP Application No. 06015782.3/ EP Patent No. 1712225, dated Jan. 26, 2012, forwarding Actavis Group PTC EHF's Jan. 5, 2012, submission.
European Patent Office, Communication of a notice of opposition for EP Application No. 06015782.3/ EP Patent No. 1712225, dated Jan. 26, 2012, forwarding Chemo Iberica, S.A.'s Jan. 6, 2012, submission.
European Patent Office, Communication of a notice of opposition for EP Application No. 06015782.3/ EP Patent No. 1712225, dated Jan. 26, 2012, forwarding Helm AG's Jan. 6, 2012, submission.
European Patent Office, Communication of a notice of opposition for EP Application No. 06015782.3/ EP Patent No. 1712225, dated Jan. 26, 2012, forwarding Hexal AG's Jan. 4, 2012, submission.
European Patent Office, Communication of a notice of opposition for EP Application No. 06015782.3/ EP Patent No. 1712225, dated Jan. 26, 2012, forwarding Pentafarma S.A.'s Jan. 5, 2012, submission.
European Patent Office, Communication of a notice of opposition for EP Application No. 06015782.3/ EP Patent No. 1712225, dated Jan. 26, 2012, forwarding Sanovel ILAC Sanayi VE Ticaret A.S.'s Jan. 3, 2012, submission.
European Patent Office, Communication of a notice of opposition for EP Application No. 06015782.3/ EP Patent No. 1712225, dated Jan. 26, 2012, forwarding Stada Arzneimittel AG's Jan. 3, 2012, submission.
European Patent Office, Communication of a notice of opposition for EP Application No. 06015782.3/ EP Patent No. 1712225, dated Jan. 26, 2012, forwarding Teva Pharmaceutical Industries Ltd.'s Jan. 5, 2012, submission.
European Patent Office, Summons to attend oral proceedings pursuant to Rule 115(1) EPC, EP Patent No. 1419776, Oct. 25, 2011.
Glick et al., "Treatment with atypical antipsychotics: new indications and new populations," Journal of Psychiatric Research, 35:187-191 (2001).
Guille et al., "A Naturalistic Comparison of Clozapine, Risperidone, and Olanzapine in the Treatment of Bipolar Disorder," J. Clin. Psychiatry, 61(9):638-642 (2000).
International Standard, "Particle size analysis—Laser diffraction methods," ISO 13320-1:1999(E) (1999).
International statistical classification of diseases and related health disorders, 10th revision (ICD-10), vol. 1—Systematic directory, p. 281, 2010.

(56) References Cited

OTHER PUBLICATIONS

Jordan et al., "The antipsychotic aripiprazole is a potent, partial agonist at the human 5-HT1A receptor," European Neuropsychopharmacol., 11(suppl. 3):S268 (2001).
Keck et al., "Anticonvulsants and Antipsychotics in the Treatment of Bipolar Disorder," J. Clin. Psychiatry, 59(suppl. 6):74-81 (1998).
Keck et al., "Antipsychotics in the Treatment of Mood Disorders and Risk of Tardive Dyskinesia," J. Clin. Psychiatry, 61(suppl. 4):33-38 (2000).
Leo & Del Regno, "Atypical Antipsychotic Use in the Treatment of Psychosis in Primary Care," Primary Care Companion J. Clin. Psychiatry, 2(6):194-204 (2000).
Mar. 1, 2012, Communication from European Patent Office, forwarding Teva Pharmaceutical Industries Ltd.'s Feb. 24, 2012, submission including DYC1 (Declaration of Professor Boese together with Enclosures I and II), DYC2 (Annex III of DYC1), and DYC3 (Repetition of D3, p. 938 final paragraph, lines 1-3).
Mar. 5, 2012, Communication from European Patent Office, forwarding letter from opponent O1, Teva Pharmaceutical Industries Ltd., dated Feb. 28, 2012, regarding Opposition to EP Patent No. 1419776B, including a signed version of Experimental Report DYC3 and Annexes 1 and 2.
Nikkiso, "Microtrac particle distribution analyzers," http://www.nikkiso-b.co.jp/product_file/product1.htm, printed Jul. 20, 2007.
Ozdemir, "Aripiprazole Otsuka Pharmaceutical Co Ltd," Current Opinion in CPNS Investigational Drugs, 2(1):105-111 (2000).
Ray, "CINP 2000—Collegium Internationale Neuro-Psychopharmacologicum 22nd Congress," Drugs, 3(9):1023-1025 (2000) (abstract).
Sachs et al., "The Expert Consensus Guideline Series, Medication Treatment of Bipolar Disorder 2000," A Postgraduate Medicine Special Report, pp. 1-20, Apr. 2000.
Stahl, "Dopamine System Stabilizers, Aripiprazole, and the Next Generation of Antipsychotics, Part 1—'Goldilocks' Actions at Dopamine Receptors," J. Clin. Psychiatry 62(11):841-842 (2001).
Stahl, "Dopamine System Stabilizers, Aripiprazole, and the Next Generation of Antipsychotics, Part 2—Illustrating Their Mechanism of Action," J. Clin. Psychiatry 62(12):923-924 (2001).
Stahl, Essential Psychopharmacology of Depression and Bipolar Disorder, Ed. 1, Cambridge University Press, p. 148, 2000.
Tamminga & Lahti, "Treatments for chronic psychosis," Dialogues in Clinical Neuroscience, 3(4):281-291 (2001).
Tohen & Zarate, "Antipsychotic Agents and Bipolar Disorder," J. Clin. Psychiatry, 59(suppl. 1):38-48 (1998).
Wedd, "Determination of Particle Size Distribution Using Laser Diffraction," Educ. Reso. for Part. Techn., 032Q-Wedd (2003).
"Aripiprazole OPC 14597," Drugs R & D, 2(1):47-48 (1999).
Abe et al., "Effect of 5-{3-[((2,S)-1,4-Benzodioxan-2-ylmethyl)amino]propoxy}-1,3-benzodioxole HCl (MKC-242), a Novel 5-$HT_{1A}$-Receptor Agonist, on Aggressive Behavior and Marble Burying Behavior in Mice," Jpn. J. Pharmacol., 76:297-304 (1998).
Abou-Gharbia et al., "Synthesis and Structure-Activity Relationship of Substituted Tetrahydro- and Hexahydro-1,2-benzisothiasol-3-one 1,1-Dioxides and Thiadiazinones: Potential Anxiolytic Agents," J. Med. Chem., 32(5):1024-1033 (1989).
Abraham et al., "LSD-Like Panic From Risperidone in Post-LSD Visual Disorder," Journal of Clinical Psychopharmacology, 16(3):238-241 (1996).
Aceto et al.., "Suppression of Opiate Withdrawal and Cocaine Hyperarousal Syndromes by Buspirone," Arzneim.-Forsch./Drug Res., 43 (II), Nr. 9, pp. 942-945 (1993).
Affidavit of Professor Cools (2008), pp. 1-5.
Agmo et al., "Dopamine and Sexual Behavior in the Male Rabbit," Pharmacol. Biochem. Behav., 55:289-295 (1996).
Agnew et al., "Dorlands illustrated medical dictionary, 24th Edition," 1965, W:B: Saunders Company, Philadelphia, p. 1088.
Aguirre, Introduccion a la Tecnologia Farmaceutica, vol. 1, pp. 92, 96, and 117 (1989).
Ahlenius et al., "Effects of Selective Dopamine $D_1$ and $D_2$ Antagonists on Male Rat Sexual Behavior," Experientia, 46:1026-1028 (1990).
Ahlenius et al., "Specific Involvement of Central 5-$HT_{1A}$ Receptors in the Mediation of Male Rat Ejaculatory Behavior," Neurochemical Research, 22(8):1065-1070 (1997).
Ajit, "Does Aripiprazole Have a Role in Treating Cognitive Impairment in Parkinson's Disease," J. Neuropsychiatry Clin. Neurosci., 19(2):205-206 (2007).
Alfieri et al., "Comparative efficacy of a single oral dose of ondansetron and of busipirone against cisplatin-induced emesis in cancer patients," British Journal of Cancer, 72:1013-1015 (1995).
Amended Statement of Grounds of Opposition filed Mar. 17, 2011, for Australian Patent No. 2007201701 by Alphapharm Pty. Ltd.
American Psychiatric Association, "DSM-IV-TR," Diagnostic and Statistical Manual of Mental Disorders, Fourth Edition, "Mood disorders", 345-428 (2000).
Aoki et al., "Study on Crystal Transformation of Aripiprazol"; 4th Japanese-Korean Symposium on Separation Technology, pp. 937-940, (1996).
Aouizerate et al., "Updated Overview of the Putative Role of the Serotoninergic System in Obsessive-compulsive Disorder," Neuropsychiatric Disease and Treatment, 1(3):231-243 (2005).
Apr. 10, 2008, Communication from the European Patent Office forwarding Notices of Opposition submitted by Teva Pharmaceutical Ind., Ltd. and Stada Arzneimittel AG.
Apr. 12, 2010, Communication from European Patent Office, forwarding a letter from opponent 01, Teva Pharmaceutical Industries Limited, dated Mar. 29, 2010, regarding the Appeal of EP Patent No. 1330249.
Apr. 12, 2010, Communication from European Patent Office, forwarding a letter from opponent 03, Pharmaceutical Works Polpharma, dated Mar. 22, 2010, regarding the Appeal of EP Patent No. 1330249, including Documents D15a (Experimental Results(D15) Obtained in 2006), D15b (Further data from experimental results as obtained by Opponent 03 in 2006), and D15c (Experimental results (D15c)—a Second Series of experiments).
Apter et al., "Buspirone: Future Directions," Journal of Clinical Psychopharmacology, 19(1):86-93 (1999).
Arkle et al., "Ipsapirone Suppresses Food Intake in Food-Deprived Rats by an Action at 5-$HT_{1A}$ Receptors," European Journal of Pharmacology, 408:273-276 (2000).
Aulton, Pharmaceutics: The Science of Dosage Form Design, Churchill Livingstone, Edinburgh, 1988, pp. 8-9 and 223-226.
Banov et al., "Clozapine Therapy in Refractory Affective Disorders: Polarity Predicts Response to Long-Term Follow-Up," J. Clin. Psychiatry, 55(7):295-300 (1994) (Abstract).
Bartoszyk, "Anxiolytic Effects of Dopamine Receptor Ligands: I. Involvement of Dopamine Autoreceptors," Life Sciences, 62:649-663 (1998).
Bauer et al., "Pharmazeutische Technologie," Georg Thieme Verlag, Stuttgart, pp. 75 81 (1986).
Beers, M.D. et al., "The Merck Manual of Diagnosis and Therapy, seventeenth edition" Merck Research Laboratories, Whitehouse Stations, N.J., pp. 1513-1516, (1999).
Bjorvatn et al., "Sleep/waking effects of a selective 5-$HT_{1A}$ receptor agonist given systemically as well as perfused in the dorsal raphe nucleus in rats," Brain Research, 770:81-88 (1997).
Boast et al., "5HT Antagonists Attenuate MK801-Impaired Radial Arm Maze Performance in Rats," Neurobiology of Learning and Memory, 71, pp. 259-271 (1999).
Bristol-Myers Squibb Press Release, "New Data Presented Today at American Psychiatric Association Annual Meeting," May 22, 2002.
Brittain, "Polymorphism in Pharmaceutical Solids," Drugs and the Pharmaceutical Science, vol. 95, Chapter entitled: "Methods for the Characterization of Polymorphs—X-Ray Powder Diffraction," pp. 235-238, 1999.
Brittain, "Polymorphism in Pharmaceutical Solids," New York, pp. 334-335 (1999).
Brittain, "Spectral Methods for the Characterization of Polymorphs and Solvates," Journal of Pharmaceutical Sciences, 86(4):405-412 (1997).

(56) References Cited

OTHER PUBLICATIONS

Brittain, Polymorphism in Pharmaceutical Solids, Marcel Dekker, Inc., New York, 1999, pp. 235-237 and 270-271.
Buckley et al., "When Symptoms Persist: Clozapine Augmentation Strategies," Schizophrenia Bulletin, 27(4):615-628 (2001).
Caira, "Crystalline Polymorphism of Organic Compounds," pp. 165-166, (1988).
Canive et al., "Spontaneous Brain Magnetic Activity in Schizophrenia Patients Treated With Aripiprazole," Psychopharmacol Bull, 34(1):101-5 (1998).
Carli et al., "S 15535, a benzodioxopiperazine acting as presynaptic agonist and postsynaptic $5\text{-HT}_{1A}$ receptor antagonist, prevents the impairment of spatial learning caused by intrahippocampal scopolamine," British J. Pharmacology, 128:1207-1214 (1999).
Carli et al., "Stimulation of $5\text{-HT}_{1A}$ receptors in the dorsal raphe reverses the impairment of spatial learning caused by intrahippocampal scopolamine in rats," European J. Neuroscience, 10:221-230 (1998).
Certified English translation of Planowski et al. Procesy i paraty w technologii chemiczej, WNT, Warswa (1974) p. 765-771.
Cervo et al., "Effects of dopaminergic and glutamatergic receptor antagonists on the establishment and expression of conditioned locomotion to cocaine in rats," Brain Research, 739:31-38 (1996).
Clifton et al., "Stimulation and Inhibition of Food Intake by the Selective Dopamine $D_2$ Agonist, N-0437: A Meal Pattern Analysis," Pharmacol. Biochem. Behav, 33:21-26 (1989).
Cole et al., "$5\text{-HT}_{1A}$ receptor agonists improve the performance of normal and scopolamine-impaired rats in an operant delayed matching to position task," Pyschopharmacology, 116:135-142 (1994).
Communication from European Patent Office dated Jul. 8, 2010, forwarding Maiwald's statement setting forth grounds of appeal for European Application Patent No. 05023971.4 (EP 1 621 198) dated Jun. 29, 2010.
Comparison of PXRD spectra; Hydrate A and MAB-1541-w—matching scales; attached to Opposition submitted by Opponent I Teva Pharmaceuticals and transmitted by European Patent Office on Apr. 27, 2009, in EP Patent No. 1 330 249.
Comparison of PXRD spectra; Hydrate A and MAB-1541-w—spectra aligned to take account of systematic error attached to Opposition submitted by Opponent I Teva Pharmaceuticals and transmitted by European Patent Office on Apr. 27, 2009, in EP Patent No. 1 330 249.
Connor et al., "The Use of Aripiprazole in Obsessive-Compulsive Disorder: Preliminary Observations in 8 Patients," J. Clin. Psychiatry, 66(1):49-51 (2005).
Correll, "Assessing and Maximizing the Safety and Tolerability of Antipsychotics Used in the Treatment of Children and Adolescents," J. Clin. Psychiatry, 69(Supp 4):26-36 (2008).
Cuesta et al., "Effects of Olanzapine and Other Antipsychotics on Cognitive Function in Chronic Schizophrenia: A longitudinal Study," Schizophrenia Research, 48:17-28 (2001).
Ebenezer et al., "Effects of the $5\text{-HT}_{1A}$ Receptor Agonist 8-OH-DPAT on Operant Food Intake in Food-Deprived Pigs," Physiology & Behavior, 67(2):213-217 (1999).
Ecuadorian Institute of Intellectual Property Patentability Examination Report for Application No. SP06 6521, dated Sep. 5, 2008.
Ecuadorian Institute of Intellectual Property Patentability Examination Report for Application No. SPO6 6522, dated Sep. 19, 2008.
Elvevag et al., "Cognitive Impairment in Schizophrenia Is the Core of the Disorder," Critical Reviews in Neurobiology, 14(1):1-21 (2000).
English abstract of JP 54-130587 published Oct. 9, 1979.
English abstract of JP 56-46812 published Apr. 28, 1981.
English translation of Aripiprazol Experimental Report by Dr. Schmidt, Dec. 23, 2006.
English translation of Aripiprazol Experimental Report by Dr. Striegel, Dec. 21, 2006.
English translation of communication from European Patent Office dated Jul. 8, 2010, forwarding Maiwald's statement setting forth grounds of appeal for European Application Patent No. 05023971.4 (EP 1 621 198) dated Jun. 29, 2010.

English translation of European Patent Office Submission of Ratiopharm GMBH in Opposition to European Patent No. 1330249, transmitted Jul. 2, 2010.
English translation of European Patent Office Submission of Ratiopharm GMBH in Opposition to European Patent No. 1330249, transmitted Jul. 21, 2010, submitting Projektbericht Aripiprazol by Roland Boese and Carsten Schauerte (Document D37 referenced in the European Patent Office Submission of Ratiopharm GMBH in Opposition to European Patent No. 1330249, transmitted Jul. 2, 2010).
English translation of Examination Report Aripiprazole by Roland Boese, dated May 31, 2010, (Document D36 referenced in the European Patent Office Submission of Ratiopharm GMBH in Opposition to European Patent No. 1330249, transmitted Jul. 2, 2010).
English translation of Laboratory Report by Ratiopharm, dated Sep. 22, 2008 (Document D38 referenced in the European Patent Office Submission of Ratiopharm GMBH in Opposition to European Patent No. 1330249, transmitted Jul. 2, 2010).
English translation of Notice of Information Disclosure by Third Party issued by the Japanese Patent Office in Japanese Patent Application No. 2007-179275 on May 31, 2010.
English translation of Novelty Search Report from Hungarian Application No. P0600141, dated Feb. 19, 2008.
English translation of Office Action in Taiwanese Patent Application No. 098116881 dated May 17, 2010.
English translation of Russian Patent Office Submission of Egis Gyógyszergyár Nyrt in Opposition to Russian Patent No. 2259366 (Application No. 2003101334), including Enclosure 1, transmitted Oct. 5, 2011.
English translation of Technical Opinion 1907 from the Colombian Superintendence of Industry and Trade, dated Jul. 3, 2009.
English translation of Technical Opinion 2309 from the Colombian Superintendence of Industry and Trade, dated Dec. 28, 2007.
English translation of the Office Action from Japanese Patent Office issued in Japanese Patent Application No. 2007-179275 on Apr. 13, 2011.
English translation of the Office Action from Japanese Patent Office issued in Japanese Patent Application No. 2007-179275 on Oct. 22, 2010.
European Medicines Agency report on aripiprazole, 2005.
European Patent Office Communication of a notice of opposition for EP Application No. 04002427.5-2101/ EP Patent No. 1419776, dated Jan. 19, 2011, forwarding Teva Pharmaceutical Industries Ltd.'s Jan. 13, 2011, submission including Experimental Report 1 and Annexes 1-3.
European Patent Office Decision revoking European Patent No. EP-B-1330249 and Provision of the minutes of the oral proceedings, Jul. 7, 2009.
European Patent Office Submission of Egis Gyógyszergyár Nyrt in Opposition to European Patent No. 1330249B1, transmitted Apr. 27, 2009.
European Patent Office Submission of Ratiopharm GMBH in Opposition to European Patent No. 1330249, transmitted Jul. 2, 2010.
European Patent Office Submission of Ratiopharm GMBH in Opposition to European Patent No. 1330249, transmitted Jul. 21, 2010, submitting Projektbericht Aripiprazol by Roland Boese and Carsten Schauerte (Document D37 referenced in the European Patent Office Submission of Ratiopharm GMBH in Opposition to European Patent No. 1330249, transmitted Jul. 2, 2010).
European Patent Office Submission of Teva Pharmaceutical Ind., Ltd., submitting facts and arguments in the appeal of European Patent Application No. 05023971.4 (EP 1 621 198), dated Jun. 29, 2010.
European Patent Office Submission of Teva Pharmaceutical Industries Limited in Opposition to European Patent No. 1330249, dated Apr. 18, 2008.
European Patent Office, Summons to attend oral proceedings pursuant to Rule 115(1) EPC, EP Patent No. 1330249, Jan. 27, 2009.
European Patent Office, Summons to attend oral proceedings pursuant to Rule 115(1) EPC, EP Patent No. 1621198, Oct. 13, 2009.
Examination Report Aripiprazole by Roland Boese, dated May 31, 2010 (Document D36 referenced in the European Patent Office Submission of Ratiopharm GMBH in Opposition to European Patent No. 1330249, transmitted Jul. 2, 2010).

(56) References Cited

OTHER PUBLICATIONS

Examiner's Re-examination Report dated Jan. 28, 2009, for Australian Patent No. 2002226752.
Examiner's Re-examination Report dated Jan. 28, 2009, for Australian Patent No. 2002334413.
Examiner's Re-examination Report dated Jan. 28, 2009, for Australian Patent No. 2005201772.
Examiner's Re-examination Report dated Oct. 10, 2006, for Australian Patent No. 2002334413.
Experimental Report (Aripiprazole Hydrate A), D4 from EPO Decision of Jul. 7, 2009, regarding Application No. 02782507.4-2101/1330249.
Experimental Results (D3) provided by Opposition—Pharmaceutical Works Polpharma, transmitted Jan. 16, 2007, by European Patent Office, Application No. 02782507.4-2101/1330249.
Farah, "Atypicality of Atypical Antipsychotics", Prim. Care Companion, J. Clin. Psychiatry, 7:268-274, 2005.
Fedoroff, "Buspirone Hydrochloride in the Treatment of an Atypical Paraphilia," Archives of Sexual Behavior, 21(4):401-406 (1992).
Ferrari et al., "The Selective $D_2$ Dopamine Receptor Antagonist Eticlopride Counteracts the Ejaculatio Praecox Induced by the Selective $D_2$ Dopamine Agonist SND 919 in the Rat," Life Sciences, 55(14):1155-1162 (1994).
Findling et al., "An open clinical trial of risperidone monotherapy in young children with autistic disorder," Psychopharmacol. Bull., 33(1):155-159 (1997) (Abstract).
Findling et al., "Aripiprazole in Children with Attention-Deficit/Hyperactivity Disorder," J. Child and Adolescent Psychopharma., 18(4):347-354 (2008).
Forbes et al., "(R)-3, N-Dimethyl-N-[1-Methyl-3-(4-Methyl-Piperidin-1-yl)Propyl]Benzenesulfonamide: The First Selective 5-$HT_7$ Receptor Antagonist"; Journal of Medical Chemistry, 41(5):655-657 (1998).
Foreman et al., "Preclinical Studies on LY228729: A Potent and Selective Serotonin$_{1A}$ Agonist," Journal of Pharmacology and Experimental Therapeutics, 267(1):58-71 (1993).
Fratta et al., "Stress-induced insomnia: opioid-dopamine interactions," European Journal of Pharmacology, 142:437-440 (1987).
Friedman et al., "Open-Label Flexible-Dose Pilot Study to Evaluate the Safety and Tolerability of Aripiprazole in Patients with Psychosis Associated with Parkinson's Disease," Movement Disorders, 21(12):2078-2081 (2006).
Frye et al., "Clozapine in bipolar disorder: treatment implications for other atypical antipsychotics," Journal of Affective Disorders, 48:91-104 (1998).
Fujii et al., "Sexual Dysfunction in Japanese Patients with Schizophrenia Treated with Antipsychotics," Prog. Neuropsychopharmacol. Biol. Psychiatry, Nov. 28, 2009, issue 1878-4216.
Furniss et al., Vogel's Textbook of Practical Organic Chemistry, 5th Ed., pp. 149-151, 1989.
Galeotti et al., "Role of 5-$HT_{1A}$ Receptors in Mouse Passive Avoidance Paradigm," Jpn. J. Pharmacol., 84:418-424 (2000).
Garattini et al., "Progress in Assessing the Role of Serotonin in the Control of Food Intake," Clin. Neuropharmacol., 11(suppl. 1):S8-S32 (1988).
Garcia-Anaya et al., Los Antipsycoticos atipicos: Una Revision, Salud Mental, 24(5):37-43 (2001).
Gelernter et al., "$D_2$ Dopamine Receptor Gene (DRD2) Allele and Haplotype Frequencies in Alcohol Dependent and Control Subjects: No Association with Phenotype or Severity of Phenotype," Neuropsychopharmacology, 20:640-649 (1999).
Gelernter et al., "No Association Between $D_2$ Dopamine Receptor (DRD2) Alleles or Haplotypes and Cocaine Dependence or Severity of Cocaine Dependence in European-and African-Americans," Biol. Psychiatry, 45:340-345 (1999).
Gentile, "A Systematic Review of Quality of Life and Weight Gain-related Issues in Patients Treated for Severe and Persistent Mental Disorders: Focus on Aripiprazole," Neuropsychiatric Disease and Treatment, 5:117-125 (2009).

Geretsegger et al., "Ipsapirone in the Treatment of Bulimia Nervosa: An Open Pilot Study," International Journal of Eating Disorders, 17(4):359-363 (1995).
Giannini et al., "Behavioral Response to Buspirone in Cocaine and Phencyclidine Withdrawal," Journal of Substance Abuse Treatment, 10:523-527 (1993).
Goldman-Rakic et al., "$D_1$ Receptors in Prefrontal Cells and Circuits," Brain Research Reviews, 31:295-301 (2000).
Goodnick et al., "Aripiprazole: Profile on efficacy and safety," Expert Opinion on Pharmacotherapy, 3(12):1173-1781 (2002).
Haensel et al., "Flesinoxan: a prosexual drug for male rats," European Journal of Pharmacology, 330:1-9 (1997).
Hammerstad et al., "Buspirone in Parkinson's Disease," Clin. Neuropharmacol., 9(6):556-60 (1986).
Hamon et al., "Alterations of Central Serotonin and Dopamine Turnover in Rats Treated with Ipsapirone and Other 5-Hydroxytryptamine$_{1A}$ Agonists with Potential Anxiolytic Properties," J. Pharmacol. Exp. Ther., 246(2):745-752 (1988).
Harada et al., "Aripiprazole Augmentation for a Patient With Partial Remission of Panic Disorder," J. Clin. Psychopharmacology, Letters to the Editor, 29(3):301-302 (2009).
Harwood et al., "Experimental Organic Chemistry Principles and Practice," Blackwell Scientific Publications), pp. 136-137, (1989).
Heinrichs et al., "The Quality of Life Scale: An Instrument for Rating the Schizophrenic Deficit Syndrome," Schizophrenia Bulletin, 10(3):388-398 (1984).
Heinz et al., Organikum, Organish-chemisches Grundpractikum, VEB Deutscher Verlag der Wissenschaften, Berlin, tables A.32 and A.35 and sections 1.10.2-1.10.4, 1986.
Helman, Farmacotecnia Teorica y Practice. Tomo IV. Editorial Continental, S.A., 1981, pp. 1142 and 1165.
Hoge et al., "Aripiprazole as Augmentation Treatment of Refractory Generalized Anxiety Disorder and Panic Disorder," CNS Spectr. 13(6):522-527 (2008).
Hoshino et al., "Blood Serotonin and Free Tryptophan Concentration in Autistic Children," Neuropsychobiology 11:22-27 (1984).
Inoue et al., "Differential Effects on $D_2$ Dopamine Receptor and Prolactin Gene Expression by Haloperidol and Aripiprazole in the Rat Pituitary," Molecular Brain Research, 55: 285-292 (1998).
Inoue et al., "Effects of the Novel Antipsychotic Agent 7-{4-[4-(2,3-dichlorophenyl)-1-piperazinyl]butyloxy}-3,4-dihydro-2(1H)-quinolinone (OPC-14597) on Prolactin Release from the Rat Anterior Pituitary Gland," J. Pharm. Exp. Ther., 277:137-143 (1996).
Jan. 10, 2007, Communication from the European Patent Office forwarding a Notice of Opposition submitted by Teva Pharmaceutical Industries Limited.
Jan. 11, 2007, Communication from the European Patent Office forwarding a Notice of Opposition submitted by Fermion Oy.
Jan. 15, 2007, Communication from the European Patent Office forwarding a Notice of Opposition submitted by EGIS Gyógyszergyár Nyrt.
Jan. 15, 2007, Communication from the European Patent Office forwarding a Notice of Opposition submitted by ratiopharm GmbH.
Jan. 16, 2007, Communication from the European Patent Office forwarding a Notice of Opposition submitted by Pharmaceutical Works Polypharma.
Jordan et al., "In Vivo Effects of Aripiprazole on Cortical and Striatal Dopaminergic and Serotonergic Function," European Journal of Pharmacology, 483: 45-53 (2004).
Kane et al., "Aripiprazole for Treatment-Resistant Schizophrenia: Results of a Multicenter, Randomized, Double-Blind, Comparison Study Versus Perphenazine," J. Clin. Psychiatry, 68(2):213-223 (2007).
Kane et al., "Efficacy of Aripiprazole in Psychotic Disorders: Comparison With Haloperidol and Placebo," Int J Neuropsychopharmacol, 3 (Suppl 1):Abst P01.124 (2000).
Kay et al., "The Positive and Negative Syndrome Scale (PANSS) for Schizophrenia," Schizophrenia Bulletin, 13: 261-276 (1987).
Keck et al., "Bipolar Disorder," Advances in the Pathophysiology and Treatment of Psychiatric Disorders: Implications for Internal Medicine, 85(3): 645-661 (2001).
Keck, Jr., "Treatment Advances in Bipolar Disorder—Making Up for Lost Time," Biological Psychiatry, 48(6):430-432 (2000).

(56) References Cited

OTHER PUBLICATIONS

Keck, Jr., et al., "Bipolar Disorder," Medical Clinics of North America, W.B. Saunders Company, Philadelphia, US, 3(85):645-661 (2001).

Keefe et al., "The Effects of Atypical Antipsychotic Drugs on Neurocognitive Impairment in Schizophrenia: A Review and Meta-analysis," Schizophr Bull, 25:201-222 (1999).

Kern et al., "An Open-label Comparison of the Neurocognitive Effects of Aripiprazole Versus Olanzapine in Patients With Stable Psychosis," Schizophr Res, 49(1-2); Suppl S:234 (2001).

Kern et al., "The Neurocognitive Effects of Aripiprazole: An Open-Label Comparison with Olanzapine," Psychopharmacology, 187:312-320 (2006).

Kikuchi et al., "7-{4-[4-(2,3-Dichlorophenyl)-1-Piperazinyl]Butyloxy}-3,4-Dihydro-2(1H)-Quinolinone (OPC-14597), a New Putative Antipsychotic Drug with Both Presynaptic Dopamine Autoreceptor Agonistic Activity and Postsynaptic $D_2$ Receptor Antagonistic Activity," J. Pharm. Exp. Ther., 274:329-336 (1995).

Kikuchi et al., "Pharmacological profile of OPC-14597, a novel antipsychotic drug (1): Presynaptic dopamine autoreceptor agonistic activity and postsynaptic dopamine $D_2$ receptor antagonistic activity," Japanese Journal of Pharmacology, 67(Suppl. 1):144P (1995).

Kohen & Sarcevic, "Central Sleep Apnea in a Geriatric Patient Treated with Aripiprazole," Am. J. Ther, 16(2):197-98 (2009).

Kuzmitcheva, "Powder Diffractometry in Materials Technology," part II, pp. 1-2, 75-76, 2006.

Laboratory Report by Ratiopharm, dated Sep. 22, 2008 (Document D38 referenced in the European Patent Office Submission of Ratiopharm GMBH in Opposition to European Patent No. 1330249, transmitted Jul. 2, 2010).

Laitinen, Experimental Report on Aripiprazole Batches, Dec. 18, 2006.

Lawler et al., "Interactions of the Novel Antipsychotic Aripiprazole (OPC-14597) with Dopamine and Serotonin Receptor Subtypes," Neuropsychopharmacology, 20(6):612-627 (1999).

Lieberman, "Atypical Antipsychotic Drugs as a First-Line Treatment of Schizophrenia: A Rationale and Hypothesis," Journal of Clinical Psychiatry, 57( Suppl. 11):68-71 (1996).

Lykouras et al., "Obsessive-compulsive symptoms induced by atypical antipsychotics. A review of reported cases," Progress in Neuro-Psychopharmacology & Biological Psychiatry, 27:333-346 (2003).

Lykouras et al., "Olanzapine and obsessive-compulsive symptoms," European Neuropsychopharmacology, 10:385-387 (2000).

Malhotra et al., "An Open Clinical Trial of Buspirone in Children with Attention-Deficit/Hyperactivity Disorder," J. Am. Acad. Child Adolesc. Psychiatry, 37(4):364-371 (1998).

Mallikaarjun et al., "The Pharmacokinetics, Tolerability, and Safety of Aripiprazole Following Single and Multiple Oral Dose Administration," Int J. Neuropsychopharmacol, 3 (Suppl) 1:Abst P01.123 (2000).

Manfredi et al., "Buspirone: Sedative or Stimulant Effect?" Am. J. Psychiatry, 148(9):1213-17 (1991) (abstract).

Manfredi et al., "Dr. Manfredi and Associates Reply," Am. J. Psychiatry, 150(5):845-46 (1993).

Mar. 15, 2010, Communication from European Patent Office, forwarding a letter from opponent 04, Egis Gyogyszergyar Nyrt, dated Mar. 2, 2010, regarding Appeal of EP Patent No. 1330249, including Document D33c (Microtrac Timeline with the part Legacy Microtrac Instrumentation, The Leeds & Northrup Years (1972-1993) with Series 7991, 7995, and 7997& SVR).

Matuszewich et al., "Partial antagonism of 8-OH-DPAT's effects on male rat sexual behavior with a $D_2$, but not a 5-$HT_{1A}$, antagonist," Brain Research, 820:55-62 (1999).

McCormick, "Treatment with Buspirone in a Patient with Autism," Arch. Fam. Med., 6:368-370 (1997).

McDougle et al., "A Double-blind, Placebo-Controlled Study of Risperidone in Adults with Autistic Disorder and Other Pervasive Development Disorders," Arch. Gen. Psychiatry, 55:633-641 (1998).

McDougle et al., "Atypical Antipsychotics in Children and Adolescents with Autistic and Other Pervasive Developmental Disorders," J. Clin. Psychiatry, 69(Supp 4):15-20 (2008).

McDougle et al., "Lack of efficacy of clozapine monotherapy in refractory obsessive-compulsive disorder," Am. J. Psychiatry, 152(12):1812-1814 (1995) (Abstract).

McElroy et al., "Pharmacologic Agents for the Treatment of Acute Bipolar Mania," Biol. Psychiatry, 48:539-557 (2000).

Meltzer et al., "Multisystems and Circuitry Pharmacotherapy—Single or Multiple Receptor Targets: Which are Best for Antipsychotic Drugs," Neuropsychopharmacology 23(52):S73 (2000).

Meltzer et al., "Serotonin Receptors: Their Key Role in Drugs to Treat Schizophrenia," Progress in Neuro-Psychopharmacology & Biological Psychiatry, 27:1159-1172 (2003).

Mendelson et al., "Effects of Buspirone on Sleep and Respiration," Am. Rev. Respir. Dis. 141:1527-1530 (1990).

Micheau et al., "Stimulation of 5-$HT_{1A}$ Receptors by Systemic or Medial Septum Injection Induces Anxiogenic-like Effects and Facilitates Acquisition of a Spatial Discrimination Task in Mice," Prog. Neuro-Pyschopharmacol. & Biol. Psychiat., 23:1113-1133 (1999).

Millan et al., "Improving the Treatment of Schizophrenia: Focus on Serotonin (5-$HT)_{1A}$ Receptors," J. Pharmacol. Exp. Ther., 295(3):853-61 (2000).

Mitsukuni, "Recent Trend of Development of Psychoactive Drugs (2)—Antipsychotic Drugs," Jpn. J. Psychopharmacol., 15(3):191-210 (1995).

Mohs, "Cognition in Schizophrenia: Natural History, Assessment, and Clinical Importance," Neuropsychopharmacology, 21(6):203-210 (1999).

Molewijk et al., "Conditioned ultrasonic distress vocalizations in adult male rats as a behavioural paradigm for screening anti-panic drugs," Psychopharmacology, 117:32-40 (1995).

Monti et al., "Role of Dorsal Raphe Nucleus Serotonin 5-$HT_{1A}$ Receptor in the Regulation of REM Sleep," Life Sciences, 66(21):1999-2012 (2000).

Monti et al., "Sleep and Waking in 5,7-DHT-Lesioned or (−)-Pindolol-Pretreated Rats After Administration of Buspirone, Ipsapirone, or Gepirone," Pharmacology Biochemistry and Behavior, 52(2):305-312 (1995).

Morrison & Boylд, Organic Chemistry, p. 627, 1974.

Mullins et al., "Effects of Antidepressants on 5-$HT_7$ Receptor Regulation in the Rat Hypothalamus," Neuropsychopharmacology, 21(3):352-367 (1999).

Muraviev, Technology of Medicinal Agents, vol. 1, Moscow, pp. 63-78, 114, 115, 1980.

Nagai et al., "Aripiprazole Ameliorates Phencyclidine-Induced Impairment of Recognition Memory through Dopamine $D_1$ and Serotonin 5-$HT_{1A}$ Receptors," Psychopharmacology, 202:315-328 (2009).

Nanzando's Medical Dictionary, 1990, 17th Ed. p. 1571.

Newman-Tancredi et al., "Clozapine is a partial agonist at cloned, human serotonin 5-$HT_{1A}$ receptors," Neuropharmacology, 35(1):119-121 (1996).

Newman-Tancredi et al., "Neuropharmacological Profile of Bifeprunox: Merits and Limitations in Comparison with Other Third-Generation Antipsychotics," Current Opinion in Investigational Drugs, 8(7):539-554 (2007).

Notice of Information Disclosure by Third Party issued by the Japanese Patent Office in Japanese Patent Application No. 2007-179275 on May 31, 2010.

Nousiainen, Aripiprazole—Analytical Investigation, Dec. 19, 2006.

Novelli et al., "A Molecular Investigation Suggests No Relationship Between Obsessive-Compulsive Disorder and the Dopamine $D_2$ Receptor," Neuropsychobiology, 29:61-63 (1994).

Novelty Search Report from Hungarian Application No. P0600141, dated Feb. 19, 2008.

Odagaki et al., "5-$HT_{1A}$ Receptor Agonist Properties of Antipsychotics Determined by [35S] GTPγS Binding in Rat Hippocampal Membranes," Clinical and Experimental Pharmacology and Physiology, 34:462-466 (2007).

Office Action (Ex Parte Quayle Action) in U.S. Appl. No. 12/202,201 dated Jun. 1, 2010.

(56) References Cited

OTHER PUBLICATIONS

Office Action from Japanese Patent Office issued in Japanese Patent Application No. 2007-179275 on Apr. 13, 2011.
Office Action from Japanese Patent Office issued in Japanese Patent Application No. 2007-179275 on Oct. 22, 2010.
Office Action in Japanese Application No. 2002-560616 dated Nov. 13, 2007.
Office Action in Taiwanese Patent Application No. 098116881 dated May 17, 2010.
Office Action in U.S. Appl. No. 10/333,244 dated Apr. 29, 2009.
Office Action in U.S. Appl. No. 10/333,244 dated Feb. 26, 2007.
Office Action in U.S. Appl. No. 10/333,244 dated Jun. 11, 2008.
Office Action in U.S. Appl. No. 10/876,605 dated Apr. 10, 2009.
Office Action in U.S. Appl. No. 10/876,605 dated Aug. 23, 2010.
Office Action in U.S. Appl. No. 10/876,605 dated Dec. 9, 2009.
Office Action in U.S. Appl. No. 10/876,605 dated Mar. 3, 2008.
Office Action in U.S. Appl. No. 10/876,605 dated May 16, 2007.
Office Action in U.S. Appl. No. 11/790,504 dated Sep. 29, 2009.
Office Action in U.S. Appl. No. 11/790,603 dated Dec. 28, 2009.
Office Action in U.S. Appl. No. 11/790,604 dated May 24, 2010.
Office Action in U.S. Appl. No. 11/790,605 dated Apr. 26, 2010.
Office Action in U.S. Appl. No. 11/790,606 dated Dec. 11, 2009.
Office Action in U.S. Appl. No. 11/797,019 dated Jan. 7, 2010.
Office Action in U.S. Appl. No. 11/797,019 dated Nov. 22, 2011.
Office Action in U.S. Appl. No. 11/797,024 dated Jan. 25, 2010.
Office Action in U.S. Appl. No. 11/797,024 dated Nov. 22, 2011.
Office Action in U.S. Appl. No. 11/797,030 dated Mar. 10, 2010.
Office Action in U.S. Appl. No. 11/932,795 dated Apr. 15, 2009.
Office Action in U.S. Appl. No. 11/932,795 dated Dec. 17, 2009.
Office Action in U.S. Appl. No. 11/932,795 dated Feb. 18, 2011.
Office Action in U.S. Appl. No. 11/932,795 dated Jun. 14, 2010.
Office Action in U.S. Appl. No. 12/202,192 dated Jan. 7, 2010.
Office Action in U.S. Appl. No. 12/202,201 dated Oct. 20, 2009.
Office Action in U.S. Appl. No. 12/202,208 dated Feb. 24, 2011.
Office Action in U.S. Appl. No. 12/202,208 dated Jun. 14, 2010.
Office Action in U.S. Appl. No. 12/830,740 dated May 27, 2011.
Ongini et al., "Differential Effects of Dopamine D-1 and D-2 Receptor Antagonist Antipsychotics on Sleep-Wake Patterns in the Rat," J. Pharmaco. Exp. Therap., 266:726-731 (1993).
Ongini et al., "Effects of Remoxipride, a Dopamine D-2 Antagonist Antipsychotic, on Sleep-Waking Patterns and EEG Activity in Rats and Rabbits," Psychopharmacology, 107:236-242 (1992).
Opposition in Indian Patent Application No. IN/PCT/2002/1536 dated Jan. 8, 2010, by Torrent Pharmaceuticals Ltd., including Exhibits 1A, 3A-3C, and 5 (67 pages).
Oshiro et al.; "Novel Antipsychotic Agents with Dopamine Autoreceptor Agonist Properties: Synthesis and Pharmacology of 7-[4-(4-Phenyl-1-piperazinyl)butoxy]-3,4-dihydro-2(1H)-quinolinone Derivatives;" Journal of Med. Chemistry, 41(5):658-667, (1998).
Parada et al., "Rats Self-Inject a Dopamine Antagonist in the Lateral Hypothalamus Where It Acts to Increase Extracellular Dopamine in the Nucleus Accumbens," Pharmacology Biochemistry and Behavior, 52(1):179-187 (1995).
Partial translation of Rinsyou Seisin Yakuri, "Aripiprazole," Japanese Journal of Clinical Psychopharmacology, 9:2503-2511 (2006).
Pérez, Experimental Report on Aripiprazole, Nov. 17, 2003.
Perry, Manual del Ingeniero Quimico, vol. 1, 3rd Edition, p. 1239 (1981).
Pessina et al., "Aripiprazole augmentation of serotonin reuptake inhibitors in treatment-resistant obsessive-compulsive disorder: a 12-week open-label preliminary study," Int. Clin. Psychopharmacol., 24:265-269 (2009).
Petrie., "Acute and Long-Term Efficacy and Safety of Aripiprazole: A New Atypical Antipsychotic," Schizophrenia Research, 29 (1-2):155 (1998).
Pfaus et al., "Role of Dopamine in Anticipatory and Consummatory Aspects of Sexual Behavior in the Male Rat," Behavioral Neuroscience, 105:727-743 (1991).

Planowski et al., "Procesy i aparaty w technologii chemicznej," WNT, Warsaw (1974), p. 765-771.
Poltronieri et al., "Antipanic-like Effect of Serotonin Reuptake Inhibitors in the Elevated T-maze," Behavioural Brain Research, 147:185-192 (2003).
Pomerantz, "Quinelorane (LY163502), a $D_2$ Dopamine Receptor Agonist, Acts Centrally to Facilitate Penile Erections of Male Rhesus Monkeys," Pharmacol. Biochem. Behav., 39:123-128 (1991).
Potenza et al., "Olanzapine treatment of children, adolescents, and adults with pervasive developmental disorders: an open-label pilot study," J. Clin. Psychopharmacol., 19(1):37-44 (1999) (Abstract).
Prinssen et al., "Interactions between neuroleptics and $5-HT_{1A}$ ligands in preclinical behavioral models for antipsychotic and extrapyramidal effects," Psychopharmacology, 144(1):20-29 (1999).
Privitera et al., "Clozapine in a Bipolar Depressed Patient", Am. J. Psychiatry, 150(6):986 (1993).
Puel et al., Polymorphism in Fine Organic Processes, LAGEP UMR CNRS 5007, Université Lyon 1 ESCPE. Bât. 308G, 43 Bd. du Nov. 11, 1918. F-69622 Villeurbanne, France.
Purdon, "Long-Term Treatment With Quetiapine Improves Cognitive Function in Schizophrenia," Biol. Psychiatry, 47:42 (2000).
Realmuto et al. "Clinical Effect of Buspirone in Autistic Children," J. Clin. Pyschopharmacol., 9(2):122-125 (1989).
Remington Farmacia, 1985, 17th Edition, pp. 1911-1920.
Remington Farmacia, 2000, 20th Edition, pp. 824 and 828.
Request for Re-examination of Australian Patent No. 2002226752 (Sep. 19, 2008).
Request for Re-examination of Australian Patent No. 2002334413 (Sep. 19, 2008).
Request for Re-examination of Australian Patent No. 2005201772 (Sep. 19, 2008).
Revised European Patent Office Submission of Teva Pharmaceutical Industries Ltd. in Opposition to European Patent No. 1330249B1, transmitted Apr. 27, 2009.
Rhodes, Introduction to Particle Technology, John Wiley & Sons, Chichester, 1998, pp. 69-70.
Rinsyou Seisin Yakuri, "Aripiprazole," Japanese Journal of Clinical Psychopharmacology, 9:2503-2511 (2006).
Rivas-Vazquez et al., "Atypical Antipsychotic Medications: Pharmacological Profiles and Psychological Implications," Professional Psychology: Research and Practice, 31(6):628-640 (2000).
Robinson et al., "Clinical Effects of the $5HT_{1A}$ Partial Agonists in Depression: A Composite Analysis of Buspirone in the Treatment of Depression," J. Clin. Psychopharmacol., 10(3 Suppl):67S-76S (1990).
Rosenheck et al., "A Comparison of Clozapine and Haloperidol in Hospitalized Patients with Refractory Schizophrenia," The New England Journal of Medicine, 337(12):809-815 (1997).
Rund, Br., "How Do Neuroleptics Affect Cognitive Dysfunctions in Schizophrenia?," Nord. J. Psychiatry 53(2):121-125 (1999).
Rusk et al., "Profile of the Selective Dopamine D-2 Receptor Agonist N-0437: Its Effect on Palatability-and Deprivation-Induced Feeding, and Operant Responding for Food," Physiology & Behavior, 44:545-553 (1988).
Russian Patent Office Submission of Egis Gyógyszergyár Nyrt in Opposition to Russian Patent No. 2259366 (Application No. 2003101334), including Enclosure 1, transmitted Oct. 5, 2011.
Saha et al., "Safety and Efficacy Profile of Aripiprazole, a Novel Antipsychotic," Schizophr. Res, 36(1-3):295 (1999).
Sasa et al., "Unique Pharmacological Profile of a Novel Antipyschotic Drug, Aripiprazole (OPC-14597)", CNS Drug Reviews, 3(1):24-33 (1997).
Schafer et al., "Effects of parkinsonian medication on sleep," J Neurol, 247(Suppl 4):IV/24-IV/27 (2000).
Schmidt, Aripiprazol Experimental Report and Attachments I and II, Dec. 23, 2006.
SCRIP News Letter 2000 No. 2580, p. 11 (Oct. 4, 2000).
Seidl et al., "Serotonin (5-HT) in brains of adult patients with Down Syndrome," J. Neural Transm., 57(supp):221-232 (1999).
Seifritz et al., "The $5-HT_{1A}$ agonist ipsapirone enhances EEG slow wave activity in human sleep and produces a power spectrum similar to $5-HT_2$ blockade," Neuroscience Letters 209:41-44 (1996).

(56) References Cited

OTHER PUBLICATIONS

Serper et al., "Novel Neuroleptics Improve Attentional Functioning in Schizophrenic Patients: Ziprasidone and Aripiprazole," CNS Spectrums, 2(8): 56-59 (1997).
Sheehan et al., "The Relative Efficacy of High-dose Buspirone and Alprazolam in the Treatment of Panic Disorder: A Double-blind Placebo-controlled Study," Acta Psychiatr. Scand., 88(1):1-11 (1993).
Shiah et al., "Cortisol, Hypothermic, and Behavioral Responses to Ipsapirone in Patients with Bipolar Depression and Normal Controls," Neuropsychobiology, 38:6-12 (1998).
Specification for the thermogravimetric analyzer SDT Q-600, printed on Jul. 18, 2011.
Stam et al., "Human Serotonin 5-$HT_7$ Receptor: Cloning and Pharmacological Characterisation of Two Receptor Variants," FEBS Letters 412, pp. 489-494 (1997).
Statement of Grounds of Opposition filed on Dec. 17, 2010, for Australian Patent No. 2007201701 by Alphapharm Pty. Ltd.
Statutory Declaration by James Ellsmore filed in support of the Amended Statement of Grounds of Opposition filed Mar. 17, 2011, for Australian Patent No. 2007201701 by Alphapharm Pty. Ltd (including exhibits JE1-JE8).
Statutory Declaration by Julian Parmegiani filed in support of the Amended Statement of Grounds of Opposition filed Mar. 17, 2011, for Australian Patent No. 2007201701 by Alphapharm Pty. Ltd (including exhibits JE1-JE17).
Stellman, Encyclopedia of Occupational Health and Safety, 4th Ed., p. 7811, 1998.
Stigler et al., "Case Report: Aripiprazole for Maladaptive Behavior in Pervasive Development Disorders," J. Child and Adolescent Psychopharmacology, 14(3):455-463 (2004).
Striegel, Aripiprazol Experimental Report, Dec. 21, 2006.
Sumiyoshi et al., "Tandospirone, a serotonin-1A agonist, added to neuroleptic treatment enhances cognitive performance in schizophrenia," Database accession No. PREV200200022926, Society for Nueroscience Abstracts (2001).
Summons to Attend Oral Proceedings from European Patent Office, regarding European Patent Application No. 06015782.3 (European Patent No. 1712225), dated Apr. 12, 2010.
Tamai et al., "The Clinical Efficacy of a 5-$HT_{1A}$ Agonist, SM-3997, In the Treatment of Bulimia," International Journal of Obesity, 14:289-292 (1990).
Tanninen, Test Report on Aripiprazole, Dec. 19, 2006.
Test Report No. 32 of the X-Ray Diffraction Laboratory of the National Commission of Atomic Energy, Argentina, Aug. 20, 2003.
Test Report No. 33 of the X-Ray Diffraction Laboratory of the National Commission of Atomic Energy, Argentina, dated Aug. 25, 2003.
The Merck Index—Aripiprazole, 2001.
The Merck Manual, 17th Ed., 1999, pp. 2233-2236.
The United States Pharmacopeia (USP) 29, pp. 2788-2789, (2006).
Tramontina et al., "Aripiprazole in Juvenile Bipolar Disorder Comorbid with Attention-Deficit/Hyperactivity Disorder: An Open Clinical Trial," CNS Spectr., 12(10):758-762 (2007).
Translation of Opposition Brief as submitted to the European Patent Office by patent attorneys Maiwald Patentanwaltsgesellschaft mbH, dated Feb. 25, 2008.
Tunnicliff, "Molecular Basis of Buspirone's Anxiolytic Action," Pharmacology & Toxicology, 69:149-156 (1991).
Vieta et al., "Effectiveness of Aripiprazole v. Haloperidol in Acute Bipolar Mania, Double-blind, Randomised, Comparative 12-week Trial," British Journal of Psychiatry, 187:235-242 (2005).
Vippagunta et al., "Crystalline Solids," Advanced Drug Delivery Reviews 48:3-26 (2001).
Wade & Weller., Handbook of Pharmaceutical Excipients, American Pharmaceutical Association, Washington, and The Pharmaceutical Press, London, 1994, 2nd Ed., pp. 1-2.
Wang et al., The Effect of Physical Environment of Crystallization Process on the Polymorph of Ciprofloxacin Hydrochloride, School of Chemical Engineering and Technology, Tianjin University, Tianjin,
300072, P. R. China, 15th International Symposium on Industrial Crystallization 1(2):623-628 (2002).
Ward et al., "Forebrain serotonin depletion facilitates the acquisition and performance of a conditional visual discrimination task in rats," Behavioral Brain Research, 100:51-65 (1999).
Wickrematch & Morris, "Aripiprazole Associated with Severe Exacerbation of Parkinson's Disease," Movement Disorders, 21(9):1538-1539 (2006).
Wolfgang Beckmann, "Seeding the Desired Polymorph: Background, Possibilities, Limitations, and Case Studies," Chemical Engineering Department, Chemical Development, Schering AG, 13342 Berlin, Jul. 6, 2000.
Yamada et al., Society of Neuroscience Abstracts 26 (1-2), No. 871.7 (2000).
Yau, "Impact of Adrenalectomy on 5-$HT_6$ and 5-$HT_7$ Receptor Gene Expression in the Rat Hippocampus," Molecular Brain Research 45:182-186 (1997).
Zakrzewsk & Marek, Solid State Characterization of Pharmaceuticals, 2006, pp. 134-135 and 152.
Zhang, "Regulation of the Central Opioidergic Nervous System on the Emotional State of Anxiety and its Possible Mechanisms," Sheng Li Ke Xue Jin Zhan, 28(1):41-44 (1997).
Angst et al., "Prevalence of Bipolar Disorders: Traditional and Novel Approaches," Clin. Appr. Bipol. Disord. 1:10-14 (2002).
Declaration of Markus Antonietti executed Jan. 29, 2013, during opposition proceedings for European Patent No. 1330249, including Exhibits A and B.
Declaration of Nikkiso Co., Ltd. by Yasuo Kizawa dated Feb. 7, 2013, during opposition proceedings for European Patent No. 1330249, including "Pamphlet of Microtrac HRA" and "Pamphlet of Nanotrac UPA".
Dziegilewski, "Selected Mood Disorders," DSM-IV TR in Action, 2nd Edition, pp. 297-298 (2010).
European Patent Office submission of Otsuka Pharmaceutical Co., Ltd. during opposition proceedings for European Patent No. 1330249, dated Mar. 7, 2013.
European Patent Office Submission of PENTAFARMA S.A. in Opposition to European Patent No. 1712225, dated Apr. 11, 2013, including D55 (excerpt from online Dictionary).
European Patent Office Submission of Teva Pharmaceutical Industries Ltd. in Opposition to European Patent No. 1712225, dated Apr. 12, 2013.
Partial English translation of submission of Sanovel Ilac Sanayi Ve Ticaret Anonim Sirketi in opposition to Turkish Patent No. TR2006/0246, dated Feb. 25, 2013.
Statement of Grounds and Particulars by Apotex Pty Ltd in opposition Australian Patent Application No. 2009233591, dated Feb. 21, 2013.
Submission of Sanovel Ilac Sanayi Ve Ticaret Anonim Sirketi in opposition to Turkish Patent No. TR2006/0236, dated Feb. 25, 2013.
Appeal by Egish Died'Jserdiar Nail'Jvanoshan Mukede Resven'Jtarshashag from the decision of the Arbitrazh Court of Moscow, in re Case No. A40-115364/12-12-530, issued Dec. 4, 2012.
Bazire, "Psychotropic Drug Directory 2001/02: The professionals' pocket handbook and aide memoire," pp. 78-83 (2001).
Benabarre et al., "Bipolar disorder, schizoaffective disorder and schizophrenia: epidemiologic, clinical and prognostic differences," Eur. Psychiatry 16(3):167-172 (2001) (Abstract).
Davis et al., "Ziprasidone," CNS Drugs 8(2):153-159 (1997).
European Patent Office submission of Otsuka Pharmaceutical Co., Ltd. during appeal for European Patent No. 1419776, dated Oct. 15, 2012, including enclosures D23, D24, and D25.
European Patent Office submission of Otsuka Pharmaceutical Co., Ltd. during opposition proceedings for European Patent No. 1712225, dated Nov. 5, 2012, including enclosure Table listing all cited documents, D41, D42, and D51.
European Patent Office submission of Otsuka Pharmaceutical Co., Ltd. during opposition proceedings for European Patent No. 1330249, dated Oct. 25, 2012, including enclosures D39 and D40.
European Patent Office, Summons to attend oral proceedings pursuant to Rule 115(1) EPC, EP Patent No. 1712225, Feb. 1, 2013.

(56) References Cited

OTHER PUBLICATIONS

Haddjeri et al., "Acute and long-term actions of the antidepressant drug mirtazapine on central 5-HT neurotransmission," Journal of Affective Disorders 51:255-266 (1998).
Haddjeri et al., "Increased Tonic Activiation of Rat Forebrain 5-HT1A Receptors by Lithium Addition to Antidepressant Treatments," Neuropsychopharmacology 22(4):346-356 (2000).
Haddjeri et al., "Long-Term Antidepressant Treatments Result in a Tonic Activiation of Forebrain 5-HT1A Receptors," Journal of Neuroscience 18(23):10150-10156 (1998).
Jan. 31, 2013, Communication from the European Patent Office, forwarding a letter of opponent OVI, Pentafarma S.A., dated Jan. 21, 2013, regarding opposition proceedings for European Patent No. 1712225.
Katz et al., "Comparison of risperidone and placebo for psychosis and behavioural disturbances associated with dementia: A randomized double-blind trial," Journal of Clinical Psychiatry 60(2):107-115 (1999).
Lucki, "Behavioral Studies of Serotonin Receptor Agonists as Antidepressant Drugs," J. Clin. Psychiatry 52(12 Suppl.):24-31 (1991).
Meltzer, "Evaluating the effects of antipsychotics on cognition in schizophrenia," Journal of Clinical Psychiatry 59(Suppl. 12):35-40 (1998).
Office Action in U.S. Appl. No. 13/327,607 dated Nov. 8, 2012.
Pleadings before Arbitrazh Court of Moscow case No. A40-115364/12-12-530 by Otsuka Pharmaceutical Co., Ltd. dated Nov. 20, 2012.
Reynolds, "The new antipsychotics—Some pharmacological aspects of their problems and potential," Expert Opinion on Pharmacotherapy 1(2):181-185 (2000).
Stahl et al., "Effectiveness of ipsapirone, a 5-HT-1A partial agonist, in major depressive disorder: support for the role of 5-HT-1A receptors in the mechanism of action of serotonergic antidepressants," International Journal of Neuropsychopharmacology 1:11-18 (1998).
Statement of Claims before the Arbitrazh Court of Moscow of Egish Died'Jserdiar Nail'Jvanoshan Mukede Resven'Jtarshashag on recognition of the decision of the Federal Service on intellectual property of May 17, 2012 (referenced in Pleadings before Arbitrazh Court of Moscow case No. A40-115364/12-12-530 by Otsuka Pharmaceutical Co., Ltd. dated Nov. 20, 2012).
Submission of Sanovel Ilac Sanayi Ve Ticaret Anonim Sirketi to the Office of the Honorable Judge of Istanbul 4th Civil Court for Intellectual and Industrial Property Rights in respect of the invalidation of the patent with No. TR 2006/02467 T4, dated Aug. 2, 2012.
Taylor et al., "Treatment of acute mania or hypomania," The South London and Maudsley NHS Trust 2001 Prescribing Guidelines, 6th Edition (2001).
Yeung et al., "Efficacy of aripiprazole, a novel antipsychotic, in schizophrenia and schizoaffective disorder: Results of a placebo-controlled trial with risperidone," Eur. Neuropsychopharm. 11(Suppl. 3): S259 (2001).
Addington et al., "Cognitive functioning and positive and negative symptoms in schizophrenia," Schizophrenia Research 5:123-134 (1991).
Affidavit of Bruce Sugriv Singh sworn Jan. 19, 2012, in case No. NSD 121/2012 concerning Australian Patent Nos. 2002226752 and 2005201772 (including Exhibits BSS-3 to BSS-15).
Affidavit of Christopher John Easton affirmed May 26, 2010, in case No. NSD 1116/2009 concerning Australian Patent No. 2002334413.
Affidavit of Professor Clive Allan Prestidge affirmed Oct. 12, 2009, in case No. NSD 1116/ 2009 concerning Australian Patent No. 2002334413.
Affidavit of Professor Patrick Dennistoun McGorry dated Feb. 21, 2012, in case No. NSD 121/2012 concerning Australian Patent Nos. 2002226752 and 2005201772 (including Exhibits PDM-5 to 7, PDM-9 to PDM-14).
American Psychiatric Association, "DSM-IV-TR," Diagnostic and Statistical Manual of Mental Disorders, Fourth Edition, "Pervasive Developmental Disorders," 69-75 (2000).
Aug. 9, 2012, Communication from European Patent Office, forwarding a letter from opponent 02, Stada Arzneirnittel AG, dated Aug. 6, 2012, regarding the appeal of EP Patent No. 1621198.
Australian Therapeutic Goods Administration, Australian Public Assessment Report for Aripiprazole, dated Apr. 2011.
Bochner et al., Therapeutic Guidelines: Psychotropic (version 4), 2000, pp. 1, 2, 4, and 115-122.
Burris et al., "Aripiprazole is a high affinity partial agonist at human D2 dopamine receptors," Int. J. Neuropsychopharmacol, 3 (Suppl 1):S129 (2000).
Conley et al., "Olanzapine compared with chlorpromazine in treatment-resistant schizophrenia," American Journal of Psychiatry, 155(7):914-920 (1998).
Conley et al., "Treatment-resistant schizophrenic patients respond to clozapine after olanzapine non-response," Biol. Psychiatry, 46:73-77 (1999).
Cottraux et al., "A Controlled Study of Cognitive Behavior Therapy with Buspirone or Placebo in Panic Disorder with Agoraphobia," British Journal of Psychiatry 167:635-641 (1995).
Craig & Young, "1-Benzylpiperazine," Organic Syntheses, 42:19 (1962).
Daniel et al., "Aripiprazole. a novel antipsychotic: Overview of a phase II study result," Int. J. Neuropsychopharmacol, 3 (Suppl 1):S157 (2000).
Ecuadorian Institute of Intellectual Property, Patentability Examination Report for Application No. SP034434 PCT, dated Jun. 8, 2004.
English translation of a letter from opponent 02, Stada Arzneirnittel AG, dated Aug. 6, 2012, regarding the appeal of EP Patent No. 1621198.
English translation of Ecuadorian Institute of Intellectual Property, Patentability Examination Report for Application No. SP034434 PCT, dated Jun. 8, 2004.
European Patent Office Decision revoking European Patent No. EP-B-1419776 and Provision of the minutes of the oral proceedings, Jun. 5, 2012.
European Patent Office, International Search Report for Application No. PCT/JP02/09858, dated Nov. 21, 2002.
Feb. 12, 2004, Communication from European Patent Office, forwarding third party observations regarding EP Patent Application No. 02782507.4, dated Jan. 30, 2004.
Federal Court of Australia, Judgment of J. Yates, dated Mar. 16, 2012, in case No. NSD 121/2012 concerning Australian Patent Nos. 2002226752 and 2005201772.
Federal Court of Australia, Transcript of Proceedings in case No. NSD 121/2012, dated Feb. 3, 2012, concerning Australian Patent Nos. 2002226752 and 2005201772.
Fleischhacker et al., "A double-blind, randomized comparative study of aripiprazole and olanzapine in patients with schizophrenia," Biol. Psychiatry, 65:510-517 (2009).
Further Amended Particulars of Invalidity for Australian Patent No. 2002334413, dated Jun. 15, 2011, by Apotex Pty. Ltd.
Goldberg & Gold, "Neurocognitive Deficits in Schizophrenia," in Schizophrenia (Hirsch & Weinberger eds., Blackwell Science Ltd.), 1995, pp. 146-162.
Hellewell, "Treatment-resistant schizophrenia: Reviewing the options and identifying the way forward," J. Clin. Psychiatry, 60(Suppl 23):14-19 (1999).
Hirose et al., "Efficacy and favorable side effect profile of aripiprazole determined in rats with apomorphine-induced stereotypy, catalepsy, and ptosis induction," Int. J. Neuropsychopharmacol, 3 (Suppl 1):S131 (2000).
Hustig & Norrie, "Managing schizophrenia in the community," MJA Practice Essentials—Mental Health, 57-62 (1998).
Inoue et al., "Aripiprazole, a novel antipsychotic drug, inhibits quinpirole-evoked GTPase activity but does not up-regulate dopamine D2 receptor following repeated treatment in the rat striatum," European Journal of Pharmacology 321:105-111 (1997).
Intellectual Property Office of Singapore, Search Report and Written Opinion for Singaporean Application No. 200302928-7, dated Dec. 13, 2004.

(56) References Cited

OTHER PUBLICATIONS

Jordan et al., "In Vivo Effects of Aripiprazole on Dopaminergic and Serotonergic Function in Rat Prefrontal Cortex and Striatum," Society for Neuroscience Abstracts, Society of Neuroscience, US, 2(27):2327, AN87503 (2001).
Kane et al., "Clozapine for the treatment-resistant schizophrenic," Arch. Gen. Psychiatry, 45:789-796 (1988).
Lieberman et al. (eds), Pharmaceutical Dosage Forms (Marcel Dekker Inc, 2nd revised ed.), 1989, pp. 1-130.
Meltzer, "Treatment-resistant schizophrenia—the role of clozapine," Current Medical— Research and Opinion, 14(1):1-20 (1997).
MIMS Annual 2000, "Antipsychotic agents," pp. 3-258 to 3-281.
Nikolic & Beak, "(R)-(+)-2-(Diphenylhydroxymethyl)pyrrolidine," Organic Syntheses, 74:23 (1997).
Oct. 14, 2003, Communication from European Patent Office regarding EP Patent Application No. 02782507.4.
Office Action in U.S. Appl. No. 13/067,750 dated Jul. 5, 2012.
Office Action in U.S. Appl. No. 13/067,838 dated Aug. 1, 2012.
Office Action in U.S. Appl. No. 13/185,879 dated Apr. 30, 2012.
Office Action in U.S. Appl. No. 13/195,954 dated Aug. 13, 2012.
Office Action in U.S. Appl. No. 13/327,607 dated Jun. 1, 2012.
Office Action in U.S. Appl. No. 13/426,886 dated Sep. 26, 2012.
Otsuka Pharmaceutical Co., Ltd, Additional note in support of interlocutory injunction application dated Mar. 9, 2012, in case No. NSD 121/2012 concerning Australian Patent Nos. 2002226752 and 2005201772.
Otsuka Pharmaceutical Co., Ltd, Submission in support of interlocutory injunction application dated Mar. 5, 2012, in case No. NSD 121/2012 concerning Australian Patent Nos. 2002226752 and 2005201772 (including Annexure A).
Particulars of Invalidity in case No. NSD 121/2012 for Australian Patent Nos. 2002226752 and 2005201772, dated Feb. 10, 2012, by Generic Health Pty Ltd.
Pecknold et al., "Gepirone and the Treatment of Panic Disorder: An Open Study," Journal of Clinical Psychopharmacology 13(2):145-149 (1993).
Petrie et al., "Aripiprazole, a new typical antipsychotic: Phase 2 clinical trial result," European Neuropsychopharmacology 7(Suppl 2):S227 (1997).
Statement of Grounds and Particulars dated Apr. 20, 2012, for Australian Patent Application No. 2009233591 by Apotex Pty. Ltd.
Statement of Grounds of Opposition dated Apr. 20, 2012, for Australian Patent Application No. 2009233591 by Alphapharm Pty. Limited.
Statutory Declaration of Bruce Sugriv Singh dated Mar. 14, 2012, concerning the opposition to Australian Patent Application No. 2007201701 (including Exhibits BSS-3 to BSS-8).
Vogel, Vogel's Textbook of Practical Organic Chemistry, Including Qualitative Organic Analysis (Longman Scientific & Technical, 4th revised ed.), 1987, pp. 110-125.
York, "The design of dosage forms," in Pharmaceutics: The Science of Dosage Form Design (Aulton ed., Churchill Livingston), 1988, pp. 1-13.
Rawla, "Basic Principles of Particle Size Analysis," published by Malvern Instruments, pp. 1-8 (printed from the European Patent Office with a timestamp of Jan. 4, 2007).
Excerpt from Examination Guidelines for Patent and Utlity Model in Japan, Part VII: Examination Guidelines for Inventions for Specific Fields, Ch. 3 Medicinal Inventions, p. 5, attached to the Notice of Information Disclosure by Third Party issued by Japanese Patent Office in Japanese Patent Application No. 2007-179275 on May 31, 2010) (*the Notice was cited on the SB08 filed Mar. 9, 2012 as Cite No. 223*).
English translation of excerpt from Examination Guidelines for Patent and Utility Model in Japan, Part VII: Examination Guidelines for Inventions in Specific Fields, Ch. 3 Medicinal Inventions, p. 5, attached to the Notice of Information Disclosure by Third Party issued by Japanese Patent Office in Japanese Patent Application No. 2007-179275 on May 31, 2010) (*the Notice was cited on the SB08 filed Mar. 9, 2012 as Cite No. 223*).

Aoki et al., Poster accompanying "Study on Crystal Transformation of Aripiprazol," Fourth Japanese-Korean Symposium on Separation Technology (1996).
Australian Government, IP Australia Examiner's first report on patent application No. 2002334413, dated Aug. 13, 2003.
Australian Government, IP Australia Examiner's report No. 2 on patent application No. 2002334413, dated Mar. 5, 2004.
Australian Government, IP Australia Examiner's report No. 3 on patent application No. 2002334413, dated Aug. 27, 2004.
Australian Patent Office, Search Report and Written Opinion re Application No. 200302928-7, dated Sep. 30, 2004.
European Patent Office, communication dated Dec. 13, 2005, of observations of a third party regarding EP Application No. 02782507. 4/EP Patent No. 1330249, forwarding letter dated Nov. 30, 2005.
European Patent Office, communication dated Jan. 27, 2006, of observations of a third party regarding EP Application No. 02782507. 4/EP Patent No. 1330249, forwarding letter dated Jan. 17, 2006 and documents D1 to D7.
European Patent Office, communication dated May 25, 2005, of observations of a third party regarding EP Application No. 02782507. 4/EP Patent No. 1330249, forwarding letter of Maprimed S.A. dated May 17, 2005.
Letter of Third Party dated Apr. 22, 2009, re Response of Mar. 26, 2009, to Examiner's Re-examination Report of Australian Patent No. 2002334413 dated Jan. 28, 2009.
Office Action in U.S. Appl. No. 13/067,750 dated May 22, 2013.
Office Action in U.S. Appl. No. 13/067,838 dated May 21, 2013.
Request for Re-examination of Australian Patent No. 200233413 (May 1, 2006).
Response dated Jun. 4, 2009, to Examiner's Re-Examination Report dated Jan. 28, 2009, including Third Statement of Voluntary Amendments.
Response of Mar. 26, 2009, to Re-Examination Report of Australian Patent No. 2002334413 dated Jan. 28, 2009, including Second Statement of Voluntary Amendments.
Response of Nov. 23, 2006, to Examiner's Re-examination Report of Australian Patent No. 2002334413 dated Oct. 10, 2006, including First Statement of Voluntary Amendments.
Brown et al., "Switching Outpatients With Bipolar or Schizoaffective Disorders and Substance Abuse From Their Current Antipsychotic to Aripiprazole," J. Clin. Psychiatry, vol. 66, No. 6, pp. 756-760 (2005).
English translation of petition of Sanovel Ilac Sanayi Ve Ticaret A.S. regarding Turkish patent TR 2006 02467 T4, submitted to the Istanbul 3rd Civil Court of Intellectual and Industrial Property Rights on Jun. 6, 2013.
English translation of Request for declaratory judgement on lack of infringement by Generica Ilac Sanayi Ve Tic A.S. dated Mar. 27, 2013, before the Istanbul Court on Duty for Intellectual and Industrial Rights.
European Patent Office, communication dated Jul. 16, 2013, regarding minutes of oral proceedings held Jul. 5, 2013, in Appeal No. T1772/09-3.3.01 regarding EP 1330249.
European Patent Office, communication dated May 10, 2013, forwarding letter of opponent Teva Pharmaceutical Industries Ltd dated May 6, 2013, in Appeal No. T1555/12-3.3.02 regarding EP1419776.
Meltzer et al., "Does stimulation of 5-HT1A receptors improve cognition in schizophrenia?" Behavioural Brain Research, vol. 195 pp. 98-102 (2008).
Office Action (final) in U.S. Appl. No. 13/327,607 dated Jun. 11, 2013.
Office Action in U.S. Appl. No. 13/067,838 dated Aug. 29, 2013.
Office Action in U.S. Appl. No. 13/327,618 dated Jul. 9, 2013.
Office Action in U.S. Appl. No. 13/426,886 dated May 28, 2013.
Office Action in U.S. Appl. No. 13/476,758 dated Aug. 7, 2013.
Office Action in U.S. Appl. No. 13/476,773 dated Jun. 20, 2013.
Petition of Sanovel Ilac Sanayi Ve Ticaret A.S. regarding Turkish patent TR 2006 02467 T4, submitted to the Istanbul 3rd Civil Court of Intellectual and Industrial Property Rights on Jun. 6, 2013.
Request for declaratory judgement on lack of infringement by Generica Ilac Sanayi Ve Tic A.S. dated Mar. 27, 2013, before the Istanbul Court on Duty for Intellectual and Industrial Rights.

(56) References Cited

OTHER PUBLICATIONS

Schechter et al., "The potential utility of 5-HT1A receptor antagonists in the treatment of cognitive dysfunction associated with Alzheimer's disease," Curr. Pharm. Des., vol. 8, No. 2, pp. 139-145 (2002) (Abstract).
Shapiro et al., "Aripiprazole, A novel Atypical Antipsychotic Drug with a Unique and Robust Pharmacology," Neuropsychopharmacology, vol. 28, pp. 1400-1411 (2003).
Stahl, et al., "Stahl's Illustrated Antipsychotics: Treating Psychosis, Mania and Depression," Cambridge University Press (2nd ed. 2010).
Statutory Declaration of Bruce Sugriv Singh dated Aug. 21, 2013, concerning opposition to Australian Patent Application No. 2009233591.
Statutory Declaration of Paula de Bruyn dated Aug. 21, 2013, concerning opposition to Australian Patent Application No. 2009233591.
English translation of Office Action in Japanese Patent Application No. 2011-133032 dated Feb. 28, 2014.
English translation of Office Action in Japanese Patent Application No. 2011-133033 dated Feb. 28, 2014.
English translation of Krowczynski et al., "Technologia Postaci Lekow," National Institute of Medical Publications, Warsaw, 1969, pp. 54-63, 78-81, 368-379.
European Patent Office, communication dated Mar. 10, 2014, forwarding letter of opponent Chemo Iberica, S.A. dated Mar. 5, 2014, regarding EP1712225.
European Patent Office, communication dated Mar. 27, 2014, forwarding letter of opponent Actavis Group PTC dated Mar. 20, 2014, regarding EP1712225, including document MAI8, Mutschler et al., "Mutschler Arzneimittelwirkungen: Lehrbuch der Pharmakologieund Toxikologie," 8th edition, pp. 157-172 (2001).
Krowczynski et al., "Technologia Postaci Lekow," National Institute of Medical Publications, Warsaw, 1969, pp. 54-63, 78-81, 368-379.
Merck Manual 17th ed. Japanese, Nikkei B P, p. 1569-1576, 1999.
Office Action in Japanese Patent Application No. 2011-133032 dated Feb. 28, 2014.
Office Action in Japanese Patent Application No. 2011-133033 dated Feb. 28, 2014.
Partial English translation of Merck Manual 17th ed. Japanese, Nikkei BP, p. 1569-1576, 1999.
Trunko et al., "Aripiprazole in Anorexia Nervosa and Low-Weight Bulimia Nervosa: Case Reports," International Journal of Eating Disorders, vol. 44, No. 3, pp. 269-275, 2011.
Advisory Action mailed Jun. 2, 2014, in U.S. Appl. No. 13/303,265.
Australian Government, IP Australia, Patent Examination Report No. 1 for Patent Application No. 2013203248, dated Jul. 28, 2014.
Baptista et al., "Long Term Administration of Some Antipsychotic Drugs Increases Body Weight and Feeding in Rats. Are D2 Dopamine Receptors Involved?" Pharmacology Biochemistry & Behavior, vol. 27, No. 3, pp. 399-405 (1987).
Communication to the European Patent Office, dated Oct. 24, 2014, Attachment to Submission (Auxiliary Request), regarding EP 1330249.
Communcation to the European Patent Office, dated Oct. 24, 2014, Attachment to Submission (Main Request), regarding EP 1330249.
Communication to the European Patent Office, dated Oct. 24, 2014, Letter regarding the Submission of Additional Experimental Data, regarding EP 1330249.
Communication to the European Patent Office, dated Oct. 24, 2014, Submission of Additional Experimental Data, regarding EP 1330249.
Decision of the Arbitrazh Court of the City of Moscow in Case No. A40-115364/12-12-530 dated Dec. 4, 2012.
English translation of Decision of the Arbitrazh Court of the City of Moscow in Case No. A40-115364/12-12-530 dated Dec. 4, 2012.
English translation of Examination Report in Argentine Patent Application No. P100104973, dated Nov. 6, 2014.
English translation of Hirose, "New Schizophrenia Drug Aripiprazole (OPC-14597)," Brain Science (Nou no Kagaku), vol. 20, pp. 1135-1140 (1998).

English Translation of Japanese Decision of Rejection mailed Aug. 22, 2014, JP 2011-133032 DA-05122.
English translation of List of Queries to Panel of Experts by Otsuka Pharmaceutical Co., Ltd., dated Oct. 21, 2013, to the Office of the Honorable Judge of Istanbul 3rd Civil Court of Intellectual and Industrial Property Rights in File No. 2012/200E.
English translation of Office Action in Japanese Patent Application No. 2011-133033 dated Aug. 19, 2014.
English translation of Submission of questions to experts of Sanovel Ilac Sanayi Ve Ticaret A.S. dated Oct. 21, 2013, to the Office of the Honorable Judge of Istanbul 3rd Civil Court for Intellectual and Industrial Property Rights in File No. 2012/200E.
English translation of Submission of Sanovel Ilac Sanayi Ve Ticaret A.S. dated Nov. 21, 2013, to the Office of the Honorable Judge of Istanbul 3rd Civil Court for Intellectual and Industrial Property Rights in File No. 2012/200E.
European Patent Office Decision of the Technical Board of Appeals regarding Appeal T0801/10 of Opposition to European Patent No. 1621198, dated Sep. 1, 2014.
European Patent Office Official Minutes of Oral Proceeding regarding Appeal T0801/10 of Opposition to European Patent No. 1621198, dated Jul. 8, 2014.
European Patent Office submission of Otsuka Pharmaceutical Co., Ltd. during appeal T 801/10-3.3.01 for EP1621198 dated Jan. 16, 2014.
European Patent Office submission of Otsuka Pharmaceutical Co., Ltd. regarding Appeal T0801/10 of Opposition to European Patent No. 1621198, dated Jun. 6, 2014.
European Patent Office submission of Otsuka Pharmaceutical Co., Ltd., regarding appeal T 2059/13-3.3.02 for EP1712225 dated Nov. 26, 2013.
European Patent Office Summons to Oral Proceedings regarding Appeal T0801/10 of Opposition to European Patent No. 1621198, dated Feb. 24, 2014.
European Patent Office, communication dated Jan. 28, 2014, forwarding letter of opponent Sanovel Ilac Sanayi Ve Ticaret A.S. dated Jan. 21, 2014, including exhibits WuW1 and WuW2.
European Patent Office, communication dated Jan. 28, 2014, forwarding letter of opponent Sanovel Ilac Sanayi Ve Ticaret A.S. dated Jan. 21, 2014, regarding EP1712225, including annexes WuW1 and WuW2.
European Patent Office, communication dated Mar. 20, 2014, forwarding Decision of the Technical Board of Appeal dated Jul. 5, 2013, regarding EP1330249.
Expert Report of Sanovel Ilac Sanayi Ve Ticaret A.S. dated Oct. 30, 2014, to the Office of the Honorable Judge of Istanbul 3rd Civil Court for Intellectual and Industrial Property Rights in File No. 2012/200, regarding Patent No. TR 2006/02467 T4.
Government of India, Patent Office, Communication regarding Application No. 722/KOLNP/2003, dated Aug. 29, 2014.
Hirose, "New Schizophrenia Drug Aripiprazole (OPC-14597)," Brain Science (Nou no Kagaku), vol. 20, pp. 1135-1140 (1998).
Japanese Decision of Rejection mailed Aug. 22, 2014, JP 2011-133032 (DA-05122).
Letter of Opponent (Hexal AG) regarding Appeal T2059/13 of Opposition to European Patent No. 1712225, dated Apr. 3, 2014.
Letter of Opponent (Hexal AG) regarding Appeal T2059/13 of Opposition to European Patent No. 1712225, dated Sep. 24, 2014.
Letter of Opponent (Stada Arzneimittel AG) regarding Appeal T2059/13 of Opposition to European Patent No. 1712225, dated Apr. 10, 2014.
Letter of Opponent (Teva Pharmaceutical Industries Ltd.) regarding Appeal T2059/13 of Opposition to European Patent No. 1712225, dated Apr. 14, 2014.
List of Queries to Panel of Experts by Otsuka Pharmaceutical Co., Ltd., dated Oct. 21, 2013, to the Office of the Honorable Judge of Istanbul 3rd Civil Court for Intellectual and Industrial Property Rights in File No. 2012/200E.
Notice of Appeal, Federal Court of Australia, *Apotex Ptd*. v. *Otsuka Pharmaceuticals Inc.*, dated Jun. 10, 2014, Australian Patent No. 2009233591.
Office Action (Final) mailed Dec. 20, 2013 in U.S. Appl. No. 13/303,265.

(56) References Cited

OTHER PUBLICATIONS

Office Action (Final) mailed Jun. 25, 2014, in U.S. Appl. No. 13/932,385.
Office Action in Japanese Patent Application No. 2011-133032 dated May 14, 2013.
Office Action in Japanese Patent Application No. 2011-133033 dated Aug. 19, 2014.
Office Action in Japanese Petent Application No. 2011-133033 dated May 14, 2013.
Office Action in U.S. Appl. No. 13/426,886 dated Apr. 3, 2014.
Office Action in U.S. Appl. No. 13/749,753 dated May 21, 2014.
Office Action in U.S. Appl. No. 13/932,385 dated Dec. 17, 2013.
Ohmori et al., "Late Phase II Study of Aripiprazole for Schizophrenia," JP Journal of clinical Psychopharmacology, vol. 9, No. 2, Feb. 2006.
Partial English translation of Office Action in Japanese Patent Application No. 2011-133032 dated May 14, 2013.
Partial English translation of Office Action in Japanese Patent Application No. 2011-133033 dated May 14, 2013.
Partial English translation of Yamada et al., "Effect of OPC-14597 on the stimulant-induced dopamine release in rat striatal slices," Japanese Journal of Psychopharmacology, vol. 16, p. 238 (1996).
Statutory Declaration of Jayashri Kulkarni dated Nov. 21, 2013, concerning the opposition to Australian Patent Application No. 2009233591, including Exhibit JK-7.
Submission of questions to experts of Sanovel Ilac Sanayi Ve Ticaret A.S. dated Oct, 21. 2013, to the Office of the Honorable Judge of Istanbul 3rd Civil Court for Intellectual and Industrial Property Rights in File No. 2012/200E.
Submission of Sanovel Ilac Sanayi Ve Ticaret A.S. dated Nov. 21, 2013, to the Office of the Honorable Judge of Istanbul 3rd Civil Court for Intellectual and Industrial Property Rights in File No. 2012/200E.
Yamada et al., "Effect of OPC-14597 on the stimulant-induced dopamine release in rat striatal slices.," Japanese Journal of Psychopharmacology, vol. 16, p. 238 (1996).
Kleven et al., "Modification of behavioral effects of 8-hydroxy-2-(di-n-propylamino)tetralin following chronic ethanol consumption in the rat: evidence for the involvement of 5-HT1A receptors in ethanol dependence," Euro J. of Pharmacology, vol. 281, pp. 219-228 (1995).
Massimo et al., "5-HT1A Receptor hypersensitivity in migraine is suggested by the m-chlorophenylpiperazine test," NeuroReport vol. 9, pp. 2605-2608 (1998).
De Vry et al., "Discriminative stimulus properties of the 5-HT receptor agonist 1A BAY + 3702 in the rat," Euro J. of Pharmacology, vol. 357, pp. 1-8 (1998).
Wolff et al., "Effects of a 5-HT receptor agonist on acute and delayed 1A cyclophosphamide-induced vomiting," Euro J. of Pharmacology, vol. 340, pp. 217-220 (1997).
Wolff et al., "Comparison of the Antiemetic Effects of a 5HT1A Agonist, LY228729, and 5HT3 Antagonists in the Pigeon," Pharm. Biochem. and Behavior, vol. 52, pp. 571-575 (1995).
Lucot et al., "Antiemetic effects of flesinoxan in cats: comparisons with 8-hydroxy-2-(di-n-propylamino) tetralin," Euro. J. of Pharmacology, vol. 253, pp. 53-60 (1994).
Rasmussen et al., "Chapter 1. Recent Progress In Serotonin (5-HT)1 A Receptor Modulators," in Annual Reports in Medicinal Chemistry, vol. 30, pp. 1-9 (1995).
Miyamoto et al., "Developing novel antipsychotic drugs: strategies and goals," Current Opinion in CPNS Investigational Drugs, vol. 2, pp. 25 (2000).
Conely et al., "Evaluation of Treatment>Resistant Schizophrenia," Schizophr. Bull., vol. 23, pp. 663-674 (1997).
Hagger et al., "Improvement in Cognitive Functions and Psychiatric Symptoms in Treatment-Refractory Schizophrenic Patients Receiving Clozapine," Biol. Psychiatry, vol. 34, pp. 702-712 (1993).
Sharma et al., "The Cognitive Efficacy of atypical antipsychotics in schizophrenia," J. of Clinical Psychopharm., vol. 18, pp. 12S-19S (1998).
Jann, "Clozapine," Pharmacoptherapy, vol. 11, pp. 179-195 (1991).
Lee et al., "Effects of Clozapine on Cognitive Function in Schizophrenia," J. Clin. Psychiatry, vol. 55 (Suppl. B), pp. 82-87 (1994).
Fujii et al., "Effects of Clozapine on Cognitive Functioning in Treatment-Resistant Schizophrenic Patients," J. Neuropsychiatry Clin. Neurosci, vol. 9, pp. 240-245 (1997).
Mason et al., "Clozapine has sub-micromolar affinity for 5HT receptors in human brain tissue," Eur. J. Pharmacol., vol. 221, pp. 397-398 (1992).
Hashimoto et al., "Differential changes in serotonin 5-HT1A and 5-HT2 receptor binding in patients with chronic schizophrenia," Psycho-pharmacology, vol. 112, pp. S35-S39 (1993).
Sumiyoshi et al., "Effect of adjunctive treatment with serotonion-1a agonist tandospirone on memory functions in schizophrenia," J. Clin. Pharmacol., vol. 20, pp. 386-388 (2000).
Meneses et al., "5HT1A Receptors Modulate the Consolidation of Learning in Normal and Cognitively Impaired Rats," Eur. J. Neurosci, vol. 71, pp. 207-218 (1999).
Green et al., "Does Risperidone Improve Verbal Working Memory in Treatment-Resistant Schizophrenia?" Am. J. Psychiatry, vol. 154, pp. 799-804 (1997).
Bondolifi et al., on behalf of the risperidone Study Group, "Risperidone Versus Clozapine in Treatment-Resistant Chronic Schizophrenia: A Randomized Double-Blind Study," Am. J. Psychiatry, vol. 155, pp. 499-504 (1998).
Breier et al., "Comparative Efficacy of Olanzapine and Haloperidol for Patients with Treatment-Resistant Schizophrenia," Biol. Psychiatry, vol. 45, pp. 403-411 (1999).
Bradford et al., "Atypical antipsychotic drugs in treatment-refractory schizophrenia," Psychiatry Annals, vol. 28, pp. 618-626 (1998).

METHOD OF TREATING COGNITIVE IMPAIRMENTS AND SCHIZOPHRENIAS

This is a continuation of application Ser. No. 12/830,740, filed Jul. 6, 2010, now abandoned which is a continuation of application Ser. No. 12/202,192, filed Aug. 29, 2008, now abandoned, which is a division of application Ser. No. 10/876,605, filed Jun. 28, 2004, now U.S. Pat. No. 8,030,312 which is a division of application Ser. No. 10/055,915, filed Jan. 28, 2002, now U.S. Pat. No. 7,053,092, which claims the benefit of U.S. Provisional Application No. 60/331,370, filed Jan. 29, 2001, all of which are incorporated herein by reference.

BACKGROUND OF THE INVENTION

1. Field of the Invention

The present invention relates to a method of treating a patient suffering from a-disorder of the central nervous system associated with the 5-$HT_{1A}$ receptor subtype. The active ingredient comprise a carbostyril derivative or a salt thereof.

2. Related Art

U.S. Pat. No. 5,006,528; European Patent No. 367,141 and Japanese Patent Kokai (Laid-open) 7-304,740 (1995) contain the same chemical structural formula as the carbostyril derivatives in the present invention, and their pharmacological properties are beneficial drug treatments for schizophrenia.

Carbostyril compounds, as well as those disclosed in Japanese Patent Kokai (Laid-open) 9-301,867 (1997) are useful for the treatment of anxiety.

The carbostyril derivatives disclosed in European Patent No. 226,441 have the genus of the carbostyril derivatives in the present invention, and they are useful for the treatment of hypoxia.

In addition to the above, the carbostyril derivatives disclosed in U.S. Pat. No. 4,734,416; Canadian Patent No. 1,117,110; British Patent No. 2,017,701; German Patent Nos. 2,912,105 and 2,953,723; Japanese Patent Kokai (Laid-open) Nos. 54-130,587 (1979), 55-127,371 (1980) and 62-149,664 (1987) have the genus of the carbostyril derivatives in the present invention, and they have antihistaminic activities and central nervous controlling activities.

It is reported that aripiprazole (7-{4-[4-(2,3-dichlorophenyl)-1-piperazinyl]butoxy}-3,4-dihydrocarbostyril, also known as, OPC-14597, BMS-337,039 and OPS-31) binds with high affinity to dopamine $D_2$ receptors and with moderate affinity to dopamine $D_3$ and 5-$HT_7$ receptors (Masashi Sasa et al., CNS Drug Reviews, Vol. 3, No. 1, pp. 24-33).

Further, it is reported that aripiprazole possesses presynaptic dopaminergic autoreceptor agonistic activity, postsynaptic $D_2$ receptor antagonistic activity, and $D_2$ receptor partial agonistic activity (T. Kikuchi, K. Tottori, Y. Uwahodo, T. Hirose, T. Miwa, Y. Oshiro and S. Morita: J. Pharmacol. Exp. Ther., Vol. 274, pp. 329, (1995); T. Inoue, M. Domae, K. Yamada and T. Furukawa: J. Pharmacol. Exp. Ther., Vol. 277, pp. 137, (1996)).

However, it has not been reported that compounds in the present invention have agonistic activity at 5-$HT_{1A}$ receptor subtype.

It has been reported that therapeutic interventions using 5-$HT_{1A}$ receptor ligands may be useful drug treatments for alcohol abuse (Mark Kleven et al., European Journal of Pharmacology, Vol. 281, (1995) pp. 219-228).

It is also reported that 5-$HT_{1A}$ agonist drugs may be useful for the treatment and/or prophylaxis of disorders associated with neuronal degeneration resulting from ischemic events in mammals (U.S. Pat. No. 5,162,375).

It is also reported that 5-$HT_{1A}$ receptor hypersensitivity could be the biological basis for the increased frequency of migraine attack in stressful and anxious conditions (Massimo Leone et al., Neuro Report, Vol. 9, pp. 2605-2608 (1998)).

It has recently been reported that (−)-(R)-2-[4-[[(3,4-dihydro-2H-1-benzopyran-2-yl)methyl]amino]-butyl]-1,2-benzisothiazol-3(2H)-one 1,1-dioxide monohydrochrolide (BAY-3702), a 5-$HT_{1A}$ receptor agonist, has neuroprotective, anxiolytic- and antidepressant-like effects in animal models (Jean De Vry et al., European Journal of Pharmacology, Vol. 357, (1998), pp. 1-8).

It is also reported that 5-$HT_{1A}$ receptor agonists appear to be broad spectrum antiemetic agents (Mary C. Wolff et al., European Journal of Pharmacology, Vol. 340, (1997), pp. 217-220; A B Alfieri et al., British Journal of Cancer, (1995), Vol. 72, pp. 1013-1015; Mary C. Wolff et al., Pharmacology Biochemistry and Behavior, 1995, Vol. 52, No. 3, pp. 571-575; James B. Lucot, European Journal of Pharmacology, 1997, Vol. 253, pp. 53-60).

Serotonin plays a role in several neurological and psychiatric disorders, including Alzheimer's disease, depression, nausea and vomiting, eating disorders, and migraine. (See Rasmussen et al., "Chapter 1. Recent Progress in Serotonin 5$HT_{1A}$ Receptor Modulators", in Annual Reports in Medicinal Chemistry, Vol. 30, Section I, pp. 1-9, 1995, Academic Press, Inc.). WO 00/16777 discloses that a 5$HT_{1A}$ receptor agonist, buspirone is efficacious in treating a variety of symptoms associated with ADHD, and that combined use of a D2 receptor agonist and 5-$HT_{1A}$ agonist provides effective treatments for ADHD and Parkinson's disease.

5$HT_{1A}$ agonists are effective in the treatment of cognitive impairment in Alzheimer's disease, Parkinson's disease or senile dementia. U.S. Pat. No. 5,824,680 discloses that a 5-$HT_{1A}$ agonist, ipsapirone, is effective in treating Alzheimer's disease by improving memory. U.S. Pat. No. 4,687,772 describes that a 5-$HT_{1A}$ partial agonist, buspirone, is useful for improving short term memory in patients in need of treatment. WO 93/04681 discloses that use of 5-$HT_{1A}$ partial agonists have been used for the treatment or prevention of cognitive disorders associated with Alzheimer's disease, Parkinson's disease or senile dementia.

5$HT_{1A}$ agonists are also effective in the treatment of depression. U.S. Pat. No. 4,771,053 describes that a 5-$HT_{1A}$ receptor partial agonist, gepirone, is useful in alleviation of certain primary depressive disorders, such as severe depression, endogenous depression, major depression with melancholia, and atypical depression. WO 01/52855 discloses that the combined use of the 5-$HT_{1A}$ receptor partial agonist gepirone with an antidepressant can effectively treat depression.

The 5-$HT_{1A}$ receptor partial agonist buspirone alleviates motor disorders such as neuroleptic induced parkinsonism and extrapyramidal symptoms. These observations are disclosed in U.S. Pat. No. 4,438,119. Furthermore 5-$HT_{1A}$ agonists reverse neuroleptic-induced catalepsy in rodents, which mimic movement impairments observed in Parkinson's disease (Mark J. Millan, Journal of Pharmacology and Experimental Therapeutics, 2000, Vol. 295, p 853-861). Thus, aripiprazole can be used to manage psychosis in geriatric patients, Alzheimer's disease, Parkinson's disease or senile dementia, since it possesses potent, partial agonistic activities at $D_2$ and 5-$HT_{1A}$ receptors. In addition, these patients might not experience extrapyramidal symptoms due to this property of aripiprazole.

Heretofore, schizophrenia is understood to be caused by hyperactivity in the brain dopaminergic system. For this reason, some drugs were developed with strong dopaminergic receptor blocking activity. These typical antipsychotic drugs are effective in the treatments for the positive symptoms of schizophrenia, which include hallucinations, delusions and the like. During the last decade, a variety of atypical antipsychotic drugs have been developed, which include clozapine, risperidone, olanzapine, quetiapine. These drugs have less extrapyramidal side effects, and have other activities in addition to their DA-receptor blocking activities. In contrast to typical anti-psychotic drugs, such as chlorpromazine, haloperidol, etc., it is reported that atypical antipsychotic drugs are more effective against the negative symptoms and cognitive impairments associated with schizophrenia than typical antipsychotic drugs, and atypical antipsychotic drugs also have less extrapyramidal side effects (S. Miyamoto, G. E. Duncan, R. B. Mailman and J. A. Lieberman: Current Opinion in CPNS Investigational Drugs, Vol. 2, pp. 25, (2000)). However, even though atypical antipsychotic drugs provide a suitable pharmacotherapy for schizophrenia, certain patients are resistant to the antipsychotic therapies of these drugs. These patients may either not respond or may become refractory (i.e. may feel more anxious, depressed or cognitive dysfunction) in response to antipsychotic therapy. These treatment-resistant patients pose a problem for how a physician may provide an appropriate therapy.

At present, a number of treatment-resistant and treatment-refractory schizophrenic patients display symptoms that do not respond adequately to a variety of known effective classes and doses of typical or atypical antipsychotic drugs. Furthermore, these patients may also be inveterate schizophrenia or chronic schizophrenics who are often repeatedly admitted to and discharged from hospitals (R. R. Conely and R. W. Buchanan: Schizophr. Bull., Vol. 23, pp. 663, (1997)).

Symptoms of patients corresponding to treatment-resistant and treatment-refractory schizophrenics involve not only the positive symptoms, but also the negative symptoms and emotional disorders, as well as cognitive impairments (i.e., cognitive dysfunction or cognitive disturbances) (K. Akiyama and S. Watanabe: Jpn. J. Clin. Psychopharmacol., Vol. 3, pp. 423, (2000)).

Cognitive impairment exists separately from the psychic symptoms in a schizophrenic individual. Thus, medical treatment is therefore quite important, because the cognitive impairment may disturb the socially adaptable behavior of these individuals (C. Hagger, P. Buckley, J. T. Kenny, L. Friedman, D. Ubogy and H. Y. Meltzer: Biol. Psychiatry, Vol. 34, pp. 702, (1993); T. Sharma and D. Mockler: J. Clin. Psycho-pharmacol., Vol. 18, (Supp). 1), pp. 128, (1998)).

At present, clozapine is an antipsychotic drug that is effective against treatment-resistant schizophrenia. Clozapine (marketed under the name of Clozaril) was approved in 1990 by FDA for the treatment and management of severely ill schizophrenics who failed to respond adequately to standard antipsychotic therapy (M. W. Jann: Pharmacotherapy, Vol. 11, pp. 179, (1991)). Clozapine has been reported to be effective against cognitive impairments in treatment-resistant schizophrenics (C. Hagger, P. Buckley, J. T. Kenny, L. Friedman, D. Ubogy and H. Y. Meltzer: Biol. Psychiatry, Vol. 34, pp. 702, (1993); M. A. Lee, P. A. Thompson and H. Y. Meltzer: J. Clin. Psychiatry, Vol. 55 (Suppl. B), pp. 82, (1994); D. E. M. Fujii, I. Ahmed, M. Jokumsen and J. M. Compton: J. Neuropsychiatry Clin. Neurosci., Vol. 9, pp. 240, (1997)). For example, it is reported that clozapine improves cognitive impairments in attention, response time, fluent-speech, etc. in treatment-resistant schizophrenics (M. A. Lee, P. A. Thompson and H. Y. Meltzer: J. Clin. Psychiatry, Vol. 55 (Suppl. B), pp. 82, (1994)). It has been also reported that clozapine provides effective improvements in cognitive impairments in an objective evaluation scale of the Wechsler Adult Intelligence Scale-Revised Full Scale (D. E. M. Fujii, I. Ahmed, M. Jokumsen and J. M. Compton: J. Neuropsychiatry Clin. Neurosci., Vol. 9, pp. 240, (1997)).

The $5\text{-HT}_{1A}$ receptor has been demonstrated to play a role in the therapeutic efficacy of clozapine against treatment-resistant schizophrenia and cognitive impairments. This relationship was revealed by a binding experiment using human the $5\text{-HT}_{1A}$ receptors (S. L. Mason and G. P. Reynolds: Eur. J. Pharmacol., Vol. 221, pp. 397, (1992)). Further, in accordance with progress in molecular pharmacology, it is clearly understood that $5\text{-HT}_{1A}$ receptor agonistic activity or $5\text{-HT}_{1A}$ receptor partial agonistic activity plays an important role in treatment-resistant schizophrenia and cognitive impairments (A. Newman-Tancredi, C. Chaput, L. Verriele and M. J. Millan: Neuropharmacology, Vol. 35, pp. 119, (1996)). Additionally, it was reported that the number of $5\text{-HT}_{1A}$ receptor is increased in the prefrontal cortex of chronic schizophrenics who were classified treatment-resistant. This observation was explained by a compensatory process where by the manifestation of severe symptoms of chronic schizophrenia are a result of impaired neuronal function mediated by hypofunctional $5\text{-HT}_{1A}$ receptors (T. Hashimoto, N. Kitamura, Y. Kajimoto, Y. Shirai, O, Shirakawa, T. Mita, N. Nishino and C. Tanaka: Psycho-pharmacology, Vol. 112, pp. S35, (1993)). Therefore, a lowering in neuronal transmission mediated through $5\text{-HT}_{1A}$ receptors is expected in treatment-resistant schizophrenics. Thus the clinical efficacy of clozapine may be related to its partial agonist efficacy at the $5\text{-HT}_{1A}$ receptors (A. Newman-Tancredi, C. Chaput, L. Verriele and M. J. Millan: Neuropharmacology, Vol. 35, pp. 119, (1996)). $5\text{-HT}_{1A}$ receptor agonistic activity may be related to the clinical effects of clozapine, and this hypothesis is supported by a positron emission tomography study in primates which showed that clozapine interacts with brain $5\text{-HT}_{1A}$ receptors at a therapeutically effective dose (Y. H. Chou, C. Halldin and L. Farde: Int. J. Neuropsycho-pharmacol., Vol. 4 (Suppl. 3), pp. 5130, (2000)). Furthermore tandospirone, which is known as a selective $5\text{-HT}_{1A}$ receptor agonist, improved cognitive impairments in chronic schizophrenic patients (T. Sumiyoshi, M. Matsui, I. Yamashita, S, Nohara, T. Uehara, M. Kurachi and H. Y. Meltzer: J. Clin. Pharmacol., Vol. 20, pp. 386, (2000)). While, in animal tests, all reports do not always suggest that $5\text{-HT}_{1A}$ receptor agonist activity may be related to cognitive impairment, however, 8-OH-DPAT (8-hydroxy-2-(di-n-propylamino)tetralin), which is known as a selective $5\text{-HT}_{1A}$ receptor agonist, improves learning and memory impairments induced by scopolamine known as a muscarinic receptor antagonist, suggesting a relationship between $5\text{-HT}_{1A}$ receptor agonistic activity and improvements in cognitive impairments (M. Carli, P. Bonalumi, R. Samanin: Eur. J. Neurosci., Vol. 10, pp. 221, (1998); A. Meneses and E. Hong: Neurobiol. Learn. Mem., Vol. 71, pp. 207, (1999)).

Atypical antipsychotic drugs, such as risperidone and olanzapine, were marketed after clozapine, and it is reported that these drugs improve treatment-resistant schizophrenia or cognitive impairments in treatment-resistant schizophrenics (M. F. Green, B. D. Marshall, Jr., W. C. Wirshing, D. Ames, S. R. Marder, S. McGurck, R. S. Kern and J. Mintz: Am. J. Psychiatry, Vol. 154, pp. 799, (1997); G. Bondolifi, H. Dufour, M. Patris, J. P. May, U. Billeter, C. B. Eap. and P. Baumann, on behalf of the risperidone Study Group: Am. J. Psychiatry, Vol. 155, pp. 499, (1998); A. Breier, S. H. Hamilton: Biol. Psychiatry, Vol. 45, pp. 403, (1999)).

In contrast to reports that clozapine was moderately effective against treatment-resistant schizophrenia, risperidone and olanzapine were not consistently superior to typical antipsychotic drugs in their effectiveness against treatment-resistant schizophrenia. Thus, risperidone and olanzapine bind with lower affinity to human 5-HT$_{1A}$ receptors (S. Miyamoto, G. E. Duncan, R. B. Mailman and J. A. Lieberman: Current Opinion in CPNS Investigational Drugs, Vol. 2, pp. 25, (2000)), and as such these drugs can not clearly perform activities through human 5-HT$_{1A}$ receptors at clinical effective doses.

Therefore, at present, it is understood that clozapine is effective against treatment-resistant schizophrenia (D. W. Bradford, M. H. Chakos, B. B. Sheitman, J. A. Lieberman: Psychiatry Annals, Vol. 28, pp. 618, (1998); A. Inagaki: Jpn. J. Clin. Psychopharmacol., Vol. 3, pp. 787, (2000)).

As explained above, 5-HT$_{1A}$ receptor agonistic activity is important for improving treatment-resistant schizophrenia or cognitive impairment caused by treatment-resistant schizophrenia. Clozapine is effective against treatment-resistant schizophrenia, however, its use is limited due to its severe side-effect of producing agranulocytosis which requires patients to undergo periodical blood tests. Under these circumstances, the development of a safe anti-psychotic drug with potent, full or partial agonist activity at 5-HT$_{1A}$ receptors is earnestly desired.

The carbostyril compound in the present invention binds with high affinity, and displays a potent, partial agonist activity at the 5-HT$_{1A}$ receptors and it has higher intrinsic activity (about 68%) as compared with that of clozapine. Therefore, the compound in the present invention has a 5-HT$_{1A}$ receptor agonistic activity that is more potent than the agonistic activity of clozapine. Thus, the present carbostyril compound may represent a more potent and highly safe drug for curing treatment-resistant schizophrenia, cognitive impairments caused by treatment-resistant schizophrenia, inveterate schizophrenia, cognitive impairments caused by inveterate schizophrenia, chronic schizophrenia, cognitive impairments caused by chronic schizophrenia and the like, as compared with other currently available pharmacotherapeutic treatments. That is, the compound in the present invention may prove to be a potent and safer drug therapy for treatment-resistant schizophrenia, cognitive impairments caused by treatment-resistant schizophrenia, inveterate schizophrenia, cognitive impairments caused by inveterate schizophrenia, chronic schizophrenia, or cognitive impairments caused by chronic schizophrenia, etc., which fail to respond adequately to currently available antipsychotic drugs such as chlorpromazine, haloperidol, sulpiride, fluphenazine, perphenazine, thioridazine, pimozide, zotepine, risperidone, olanzapine, quetiapine, amisulpride, etc.

In particular, the carbostyril compound in the present invention may be a potent and highly safe drug therapy against treatment-resistant schizophrenia, cognitive impairments caused by treatment-resistant schizophrenia, inveterate schizophrenia, cognitive impairments caused by inveterate schizophrenia, chronic schizophrenia or cognitive impairments caused by chronic schizophrenia, etc. which fail to respond adequately to both of 1 to 3 typical antipsychotic drugs selected from the group consisting of chlorpromazine, haloperidol and perphenazine, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairment caused by inveterate schizophrenia, chronic schizophrenia or cognitive impairment caused by chronic schizophrenia, etc. which fail to respond adequately to both of 2 typical antipsychotic drugs selected from the group consisting of chlorpromazine, haloperidol and perphenazine, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairments caused by inveterate schizophrenia, chronic schizophrenia, or cognitive impairment caused by chronic schizophrenia, etc. which fail to respond adequately to both of 1 to 2 typical antipsychotic drugs selected from the group consisting of chlorpromazine and haloperidol, and one atypical antipsychotic drug selected from the group consisting of risperidone, olanzapine, quetiapine and amisulpride.

Moreover, the compound in the present invention may be a potent and highly safe drug therapy against treatment-resistant schizophrenia, cognitive impairments caused by treatment-resistant schizophrenia, inveterate schizophrenia, cognitive impairment caused by inveterate schizophrenia, chronic schizophrenia or cognitive impairment caused by chronic schizophrenia, etc. which fail to respond adequately to both of 2 typical antipsychotic drugs selected from the group consisting of chlorpromazine and haloperidol, and one atypical antipsychotic drug selected from the group consisting of risperidone, olanzapine, quetiapine and amisulpride.

SUMMARY OF THE INVENTION

It is an object of the present invention to provide a method of treating a patient suffering from a disorder of the central nervous system associated with the 5-HT$_{1A}$ receptor subtype.

DETAILED DESCRIPTION OF THE INVENTION

As the 5-HT$_{1A}$ receptor subtype agonist compound for use in accordance with the present invention, carbostyril derivatives represented by the following formula (1) are used:

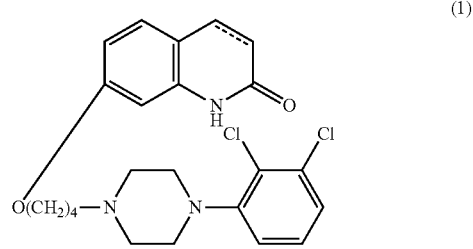

wherein the carbon-carbon bond between 3- and 4-positions in the carbostyril skeleton is a single or a double bond.

The compounds of the forgoing general formula (1) are known compounds, which are disclosed in publication such as U.S. Pat. No. 5,006,528 or which can be readily prepared by the processes described in the above publication.

The carbostyril derivative represented by the formula (1) in the present invention can easily be converted into its acid-addition salt by reacting it with a pharmaceutically acceptable acid. Examples of such acid include inorganic acids, such as hydrochloric acid, sulfuric acid, phosphoric acid, hydrobromic acid and the like; organic acids, such as oxalic acid, maleic acid, fumaric acid, malic acid, tartaric acid, citric acid, benzoic acid and the like.

The solvent of solvates is a solvent conventionally used in recrystallization. Examples of solvates include hemihydrates, hydrates, and alcoholates, such as ethanolates, methanolates, isopropanolates and the like.

The desired compounds, prepared by the reactions mentioned above, can easily be isolated and purified by usual separation procedures such as solvent extraction, dilution, recrystallization, column chromatography, preparative thin layer chromatography and the like.

The potent, partial 5-$HT_{1A}$ receptor agonist in the present invention is useful for various disorders of the central nervous system associated with the 5-$HT_{1A}$ receptor subtype that induces bipolar disorders, such as bipolar I disorder with most recent hypomanic, manic, mixed, depressed or unspecified episode; bipolar II disorder with recurrent major depressive episodes with hypomanic episodes, and cyclothymic disorder; depression, such as endogenous depression, major depression, melancholia, and treatment-resistant depression; panic disorder; obsessive compulsive disorder (OCD); sleep disorders; sexual dysfunction; alcohol abuse and drug addiction; cognitive impairment; neurodegenerative diseases, such as Alzheimer's disease, Parkinson's disease and the like, cognitive impairments caused by neurodegenerative diseases such as Alzheimer's disease, Parkinson's disease and related disorders; emesis; motion sickness; obesity; migraine; autism; Down's syndrome; attention-deficit hyperactivity disorder (ADHD); treatment-resistant, inveterate or chronic schizophrenia, (which fail to respond adequately to currently available antipsychotic drugs); cognitive impairments caused by treatment-resistant schizophrenia, inveterate schizophrenia or chronic schizophrenia and the like.

Compounds of the present invention may be suitably prepared into pharmaceutically acceptable formulations (see U.S. Pat. No. 5,006,528, European Patent No. 367,141 and Japanese Kokai (Laid-open) 7-304,740 (1995), and Japanese Patent Application No. 2000-194976 incorporated by reference herein).

The dosage of these pharmaceutical preparations of the invention may be selected appropriately depending on the method of administration, the patient's age, sex and other factors, severity of the disease and other factors. Generally, however, the daily dose of the active ingredient compound is preferably within the range of about 0.0001 to about 50 mg per kilogram of body weight. It is desirable that the active ingredient compound be contained in each unit dosage form in an amount of about 0.001 to about 1,000 mg, particularly 0.01 to 100 mg, more particularly 0.1 to 50 mg, yet more particularly 1 mg to 20 mg.

Pharmacological Tests
1. Materials and Methods
  1.1 Test Compound
  7-{4-[4-(2,3-Dichlorophenyl)-1-piperazinyl]-butoxy}-3,4-dihydrocarbostyril (aripiprazole) was used as test compound.
  1.2 Reference Compounds
  Serotonin (5-HT) and WAY-100635 (N-[2-[4-(2-methoxyphenyl)-1-piperazinyl]ethyl]-N-(2-pyridimyl)-cyclohexanecarbox amide, a 5-$HT_{1A}$ receptor antagonist, manufactured by RBI (Natick, Mass.) were used as reference compounds.
  1.3 Vehicle
  Dimethyl sulfoxide (DMSO) manufactured by Sigma Chemical Co. (St. Louis, Mo.) was used as vehicle.
  1.4 Preparation of Test and Reference Compounds
  Test compound was dissolved in 100% dimethyl sulfoxide (DMSO) to yield 100 μM stock solutions (final concentration of DMSO in all tubes containing test compound was 1%, v/v).

All other reference compounds were prepared by the same method using double-distilled water rather than DMSO.

1.5 Experimental Procedure for the [$^{35}$S]GTPγS Binding Assay
  Test and reference compounds were studied in triplicate at 10 different concentrations (0.01, 0.1, 1, 5, 10, 50, 100, 1000, 10000 and 50000 nM) for their effects upon basal [$^{35}$S]GTPγS binding to h5-$HT_{1A}$ CHO cell membranes. Reactions were performed in 5 ml glass test tubes containing 8 μl of test/reference drug mixed with 792 μl of buffer (25 mM Tris HCl, 50 mM NaCl, 5 mM $MgCl_2$, 0.1 mM EGTA, pH=7.4) containing GDP (1 μM), [$^{35}$S]GTPγS (0.1 nM) and h5-$HT_{1A}$ CHO cell membranes (10 μg protein/reaction; NEN Life Science Products, Boston, Mass.; catalog #CRM035, lot #501-60024, GenBank #X13556). Reactions proceeded for 60 min at room temperature and were terminated by rapid filtration through Whatman GF/B filter paper, using a Brandel harvester and 4×3 ml ice-cold buffer washes. $^{35}$S radio-activity bound to the filter paper was measured using liquid scintillation counting (1272 Clinigamma, LKB/Wallach).

1.6 Experimental Procedure to Determine the Binding Affinity of Test compound (aripiprazole) at the h5-$HT_{1A}$ Receptor
  Test compound was studied in triplicate at 10 different concentrations (0.01, 0.1, 1, 10, 50, 100, 500, 1000, 5000 and 10000 nM) to determine its displacement of [$^3$H] 8-OH-DPAT (1 nM; NEN Life Sciences; catalog #NET 929, lot #3406035, Specific Activity=124.9 Ci/mmol) binding to h5-$HT_{1A}$ receptors in CHO cell membranes (15-20 μg protein; NEN Life Science Products, catalog #CRM035, lot #501-60024). Membranes (396 μl) were incubated in 5 ml glass tubes containing [$^3$H] 8-OH-DPAT (396 μl), test compound or vehicle (8 μl) and buffer A (50 mM Tris.HCl, 10 mM $MgSO_4$, 0.5 mM EDTA, 0.1% (w/v) ascorbic acid, pH=7.4). All assays proceeded for 60 min at room temperature and were terminated by rapid filtration through Whatman GF/B filter paper (presoaked in buffer B; 50 mM Tris.HCl, pH=7.4), using a Brandel harvester and 4×1 ml ice-cold washes with buffer B. Non-specific binding was determined in the presence of 10 μM (+) 8-OH-DPAT.

1.7 Parameters Determined
  Serotonin (5-HT) is a full 5-$HT_{1A}$ receptor agonist which stimulates increases in basal [$^{35}$S]GTPγS binding to h5-$HT_{1A}$ receptors in recombinant CHO cell membranes. Test compound was studied at 10 concentrations to determine their effects upon basal [$^{35}$S]GTPγS binding relative to that produced by 10 μM 5-HT. The relative potency ($EC_{50}$, 95% confidence interval) and intrinsic agonist activity (% of $E_{max}$ for 10 μM 5-HT) was calculated for each compound by computerized non-linear regression analysis of complete concentration-effect data. The binding affinity of test compound at the h5-$HT_{1A}$ receptor was determined by its ability to prevent [$^3$H] 8-OH-DPAT binding to CHO cell membranes that express this receptor. Non-linear regression analysis of the competition binding data was used to calculate an inhibition constant ($IC_{50}$, 95% confidence interval), which is the concentration of test compound that occupies half of the h5-$HT_{1A}$ sites specifically bound by [$^3$H] 8-OH-DPAT. The affinity of h5-$HT_{1A}$ receptors for test compound (Ki, 95% confidence interval) was calculated by the equation, $Ki=(IC_{50})/(1+([[^3H]$ 8-OH-DPAT]/Kd), where the Kd for [$^3$H] 8-OH-DPAT at h5-$HT_{1A}$=0.69 nM (NEN Life Sciences). All estimates of drug binding affinity, potency and intrinsic efficacy at the h5-$HT_{1A}$ receptor were calculated using GraphPad Prism version 3.00 for Windows (GraphPad Software, San Diego, Calif.).

2. Results

Test compound and 5-HT produced concentration-dependent increases above basal [$^{35}$S]GTP$_\gamma$S binding. 1% DMSO tested alone had no effect upon basal or drug-induced [$^{35}$S]GTP$_\gamma$S binding.

Test compound (EC$_{50}$=2.12 nM), 5-HT (EC$_{50}$—3.67 nM), potently stimulated, basal [$^{35}$S]GTP$_\gamma$S binding. Potency and intrinsic agonist efficacy estimates were derived by non-linear regression analysis with correlation coefficients (r$^2$)>0.98 in each case (Table 1). Test compound exerted partial agonist efficacies in the 65-70% range. WAY-100635 produced no significant change (unpaired Student's t-test) in basal [$^{35}$S]GTP$_\gamma$S binding at all concentrations tested (Table 1). WAY-100635 did, however, completely inhibit the effects of 5-HT and test compound upon [$^{35}$S]GTP$_\gamma$S binding to h5-HT$_{1A}$ receptors in CHO cell membranes (Table 2). Tables 1 and 2 are shown below.

Test compound demonstrated high affinity binding to h5-HT$_{1A}$ receptors in CHO cell membranes (IC$_{50}$=4.03 nM, 95% confidence interval=2.67 to 6.08 nM; Ki=1.65 nM, 95% confidence interval=1.09 to 2.48 nM).

TABLE 1

Potency (EC$_{50}$) and Intrinsic Agonist Efficacy (E$_{max}$) of Test compound and Reference Drugs in a h5-HT$_{1A}$ [$^{35}$S]GTP$_\gamma$S CHO-cell Membrane Binding Assay.

| Drug | EC$_{50}$, nM (95% Confidence Interval) | E$_{max}$ (% ± SEM) | Goodness of Fit (r$^2$) |
|---|---|---|---|
| Test Compound | 2.12 (0.87 to 5.16) | 68.13 ± 3.16 | 0.986 |
| 5-HT | 3.67 (1.56 to 8.63) | 98.35 ± 4.47 | 0.986 |
| WAY-100635 | — | — | — |

TABLE 2

Inhibitory Potency (IC$_{50}$) of WAY-100635 versus 1 µM Concentration of 5-HT and Test compound in a h5-HT$_{1A}$ [$^{35}$S]GTP$_\gamma$S CHO-cell Membrane Binding Assay.

| Drug Combination | WAY-100635 Inhibition Potency, IC$_{50}$, nM (95% Confidence Interval) | Goodness of Fit (r$^2$) |
|---|---|---|
| 5-HT + WAY-100635 | 217.1 (127.4 to 369.7) | 0.988 |
| Test compound + WAY-100635 | 392.2 (224.1 to 686.2) | 0.989 |

What is claimed is:

1. A method of treating a patient suffering from treatment-resistant schizophrenia,
    comprising administering to said patient a therapeutically effective amount of a carbostyril compound of formula (1), or a pharmaceutically acceptable salt or solvate thereof:

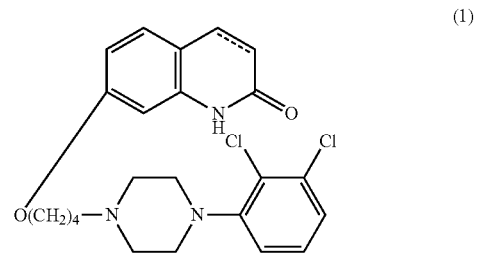

(1)

wherein the carbon-carbon bond between 3- and 4-positions in the carbostyril skeleton is a single or a double bond,
wherein the patient is a mammal and the patient fails to respond adequately to antipsychotic drugs which are at least one typical antipsychotic drug and at least one atypical antipsychotic drug selected from risperidone, olanzapine, quetiapine, and amisulpride.

2. The method of claim 1, wherein the at least one typical antipsychotic drug comprises two typical antipsychotic drugs selected from chlorpromazine, haloperidol and perphenazine.

3. The method of claim 1, wherein the at least one typical antipsychotic drug comprises one to two typical antipsychotic drugs selected from chlorpromazine and haloperidol.

4. The method of claim 1, wherein the at least one typical antipsychotic drug comprises two typical antipsychotic drugs selected from chlorpromazine and haloperidol.

5. The method according to any one of claims 1, 2, 3, and 4, wherein the carbostyril compound is 7-{4-[4-(2,3-dichlorophenyl)-1-piperazinyl]butoxy}-3,4-dihydrocarbostyril.

6. A method of treating a patient suffering from treatment-resistant schizophrenia with cognitive impairments,
    comprising administering to said patient a therapeutically effective amount of a carbostyril compound of formula (1), or a pharmaceutically acceptable salt or solvate thereof:

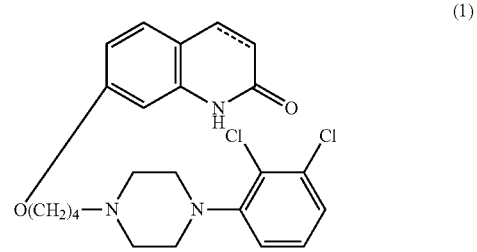

(1)

wherein the carbon-carbon bond between 3- and 4-positions in the carbostyril skeleton is a single or a double bond,
wherein the patient is a mammal and the patient fails to respond adequately to antipsychotic drugs which are at least one typical antipsychotic drug and at least one atypical antipsychotic drug selected from risperidone, olanzapine, quetiapine, and amisulpride.

7. The method of claim 6, wherein the at least one typical antipsychotic drug comprises two typical antipsychotic drugs selected from chlorpromazine, haloperidol and perphenazine.

8. The method of claim 6, wherein the at least one typical antipsychotic drug comprises one to two typical antipsychotic drugs selected from chlorpromazine and haloperidol.

9. The method of claim 6, wherein the at least one typical antipsychotic drug comprises two typical antipsychotic drugs selected from chlorpromazine and haloperidol.

10. The method according to any one of claims 6-9, wherein the carbostyril compound is 7-{4-[4-(2,3-dichlorophenyl)-1-piperazinyl]butoxy}-3,4-dihydrocarbostyril.

* * * * *